(12) United States Patent
Bakker et al.

(10) Patent No.: US 8,697,417 B2
(45) Date of Patent: Apr. 15, 2014

(54) BACULOVIRAL VECTORS COMPRISING REPEATED CODING SEQUENCES WITH DIFFERENTIAL CODON BIASES

(75) Inventors: Andrew Christian Bakker, Almere (NL); Wilhelmus Theodorus Johannes Maria Christiaan Hermens, Almere (NL)

(73) Assignee: Uniqure IP B.V., Amsterdam (NL)

( * ) Notice: Subject to any disclaimer, the term of this patent is extended or adjusted under 35 U.S.C. 154(b) by 725 days.

(21) Appl. No.: 12/670,780

(22) PCT Filed: Jul. 25, 2008

(86) PCT No.: PCT/NL2008/050512
§ 371 (c)(1), (2), (4) Date: Jun. 30, 2010

(87) PCT Pub. No.: WO2009/014445
PCT Pub. Date: Jan. 29, 2009

(65) Prior Publication Data
US 2010/0261254 A1 Oct. 14, 2010

Related U.S. Application Data

(60) Provisional application No. 60/952,081, filed on Jul. 26, 2007.

(30) Foreign Application Priority Data

Jul. 26, 2007 (EP) .................................. 07113257

(51) Int. Cl.
*C12N 7/00* (2006.01)
*C12N 7/01* (2006.01)
*C12N 7/02* (2006.01)
*C12N 5/10* (2006.01)

(52) U.S. Cl.
USPC ...... 435/235.1; 435/348; 435/239; 536/23.72

(58) Field of Classification Search
None
See application file for complete search history.

(56) References Cited

U.S. PATENT DOCUMENTS

| | | | |
|---|---|---|---|
| 5,871,974 A * | 2/1999 | Huse | ............................ 435/69.7 |
| 2003/0228696 A1 | 12/2003 | Robinson et al. | |
| 2006/0166363 A1 * | 7/2006 | Zolotukhin et al. | .......... 435/456 |
| 2009/0191597 A1 | 7/2009 | Samulski et al. | |

FOREIGN PATENT DOCUMENTS

| | | | | |
|---|---|---|---|---|
| WO | 9636712 | | 11/1996 | |
| WO | WO 0114539 A2 * | 3/2001 | | ............. C12N 15/00 |
| WO | WO 0168888 A2 * | 9/2001 | | ........... C12N 15/864 |
| WO | WO 03018820 A2 * | 3/2003 | | ........... C12N 15/864 |
| WO | WO 03061582 A2 * | 7/2003 | | |
| WO | WO 2005035743 A2 * | 4/2005 | | ............... C12N 7/01 |
| WO | 2007046703 A2 | | 4/2007 | |
| WO | 2007084773 A2 | | 7/2007 | |

OTHER PUBLICATIONS

Urabe et al. Insect Cells as a Factory to Produce Adeno-Associated Virus Type 2 Vectors. Human Gene Therapy 2002, vol. 13, pp. 1935-1943.*
Jayaraj et al. GeMS: an advanced software package for designing synthetic genes. Nucleic Acids Research 2005, vol. 33, No. 9, pp. 3011-3016.*
Hunter et al. Colocalization of adeno-associated virus Rep and capsid proteins in the nuclei of infected cells. Journal of Virology 1992, vol. 66, No. 1, pp. 317-324.*
Urabe et al., "Insect cells as a factory to produce adeno-associated virus type 2 vectors," Human Gene Therapy, 2002, 13:1935-1943.
Kohlbrenner et al., "Successful production of pseudotyped rAAV Vectors using a modified baculovirus expression system," Molecular Therapy, 2005, 12:1217-1225.
Office Action Israel (translated to English) in Corresponding Patent Application (203535) dated Feb. 12, 2012.
A. Villalobos et al., "Gene Designer: a synthetic biology tool for constructing artificial DNA segments", BMC Bioinformatics 7:285 (Jun. 6, 2006).
J. Meghrous et al., "Production of Recombinant Adeno-Associated Viral Vectors Using a Baculovirus/Insect Cell Suspension Culture System: From Shake Flasks to a 20-L Bioreactor." Biotechnol. Prog. 21:154-160 (2005).
D. Hills et al., "Baculovirus expression of human basic fibroblast growth factor from a synthetic gene: role of the Kozak consensus and comparison with bacterial expression" Biochimica et Biophysica Acta, 1260:14-28 (1995).
S. Cecchini et al., "Toward exascale production of recombinant adeno-associated virus for gene transfer applications," Gene Therapy 15:823-830 (2008).

* cited by examiner

*Primary Examiner* — Louise Humphrey
(74) *Attorney, Agent, or Firm* — Browdy and Neimark, PLLC

(57) ABSTRACT

The present invention relates to production of proteins in insect cells whereby repeated coding sequences are used in baculoviral vectors. In particular the invention relates to the production of parvoviral vectors that may be used in gene therapy and to improvements in expression of the viral rep proteins that increase the productivity of parvoviral vectors.

30 Claims, 5 Drawing Sheets

SEQUENCE LISTING

<160> NUMBER OF SEQ ID NOS: 11

<210> SEQ ID NO 1
<211> LENGTH: 1194
<212> TYPE: DNA
<213> ORGANISM: adeno-associated virus 2
<220> FEATURE:
<221> NAME/KEY: misc_feature
<223> OTHER INFORMATION: wild type

<400> SEQUENCE: 1

```
atggagctgg tcgggtggct cgtggacaag gggattacct cggagaagca gtggatccag      60
gaggaccagg cctcatacat ctccttcaat gcggcctcca actcgcggtc ccaaatcaag     120
gctgccttgg acaatgcggg aaagattatg agcctgacta aaaccgcccc cgactacctg     180
gtgggccagc agcccgtgga ggacattttcc agcaatcgga tttataaaat tttggaacta     240
aacgggtacg atccccaata tgcggcttcc gtctttctgg gatgggccac gaaaaagttc     300
ggcaagagga caccatctg gctgtttggg cctgcaacta ccgggaagac caacatcgcg     360
gaggccatag cccacactgt gcccttctac gggtgcgtaa actggaccaa tgagaacttt     420
cccttcaacg actgtgtcga caagatggtg atctggtggg aggaggggaa gatgaccgcc     480
aaggtcgtgg agtcggccaa agccattctc ggaggaagca aggtgcgcgt ggaccagaaa     540
tgcaagtcct cggcccagat agacccgact cccgtgatcg tcacctccaa caccaacatg     600
tgcgccgtga ttgacgggaa ctcaacgacc ttcgaacacc agcagccgtt gcaagaccgg     660
atgttcaaat ttgaactcac ccgccgtctg gatcatgact ttgggaaggt caccaagcag     720
gaagtcaaag acttttttcg gtgggcaaag gatcacgtgg ttgaggtgga gcatgaattc     780
tacgtcaaaa agggtggagc caagaaaaga cccgccccca gtgacgcaga tataagtgag     840
cccaaacggg tgcgcgagtc agttgcgcag ccatcgacgt cagacgcgga agcttcgatc     900
aactacgcag accgctacca aaacaaatgt tctcgtcacg tgggcatgaa tctgatgctg     960 tttcctgca gacaatgcga gaatgaat cagaattcaa atatctgctt cactcacgga    1020
cagaaagact gtttagagtg ctttcccgtg tcagaatctc aacccgtttc tgtcgtcaaa    1080
aaggcgtatc agaaactgtg ctacattcat catatcatgg gaaaggtgcc agacgcttgc    1140
```

```
actgcctgcg atctggtcaa tgtggatttg gatgactgca tctttgaaca ataa          1194
```

```
<210> SEQ ID NO 2
<211> LENGTH: 1194
<212> TYPE: DNA
<213> ORGANISM: adeno-associated virus 2
<220> FEATURE:
<221> NAME/KEY: misc_feature
<223> OTHER INFORMATION: sf9 optimized

<400> SEQUENCE: 2
atggagctgg tgggttggct ggtggacaag ggtatcacct ccgagaagca gtggatccag    60
gaggaccagg cttcctacat ctccttcaac gctgcttcca actcccgttc ccagatcaag   120
gctgctctgg acaacgctgg taagatcatg tccctgacca agaccgctcc tgactacctg   180
gtgggtcagc agcctgtgga ggacatctcc tccaaccgta tctacaagat cctggagctg   240
aacggttacg accctcagta cgctgcttcc gtgttcctgg ttgggctac caagaagttc    300
ggtaagcgta acaccatctg gctgttcggt cctgctacca ccgtaagac caacatcgct   360
gaggctatcg ctcacaccgt gcctttctac ggttgcgtga actggaccaa cgagaacttc   420
cctttcaacg actgcgtgga acagatggtg atctggtggg aggagggtaa gatgaccgct   480
aaggtggtgg agtccgctaa ggctatcctg gtggttcca aggtgcgtgt ggaccagaag   540
tgcaagtcct ccgctcagat cgaccctacc cctgtgatcg tgacctccaa caccaacatg   600
tgcgctgtga tcgacggtaa ctccaccacc ttcgagcacc agcagcctct gcaggaccgt   660
atgttcaagt tcgagctgac ccgtcgtctg gaccacgact cggtaaggt gaccaagcag   720
gaggtgaagg acttcttccg ttgggctaag gaccacgtgg tggaggtgga gcacgagttc   780
tacgtgaaga agggtggtgc taagaagcgt cctgctcctt ccgacgctga catctccgag   840
cctaagcgtg tgcgtgagtc cgtggctcag ccttccacct ccgacgctga ggcttccatc   900
aactacgctg accgttacca gaacaagtgc tcccgtcacg tgggtatgaa cctgatgctg   960
ttcccttgcc gtcagtgcga gcgtatgaac cagaactcca acatctgctt caccacggt   1020
cagaaggact gcctggagtg cttccctgtg tccgagtccc agcctgtgtc cgtggtgaag  1080
aaggcttacc agaagctgtg ctacatccac cacatcatgg gtaaggtgcc tgacgcttgc  1140
accgcttgcg acctggtgaa cgtggacctg gacgactgca tcttcgagca gtaa          1194
```

```
<210> SEQ ID NO 3
<211> LENGTH: 1194
<212> TYPE: DNA
<213> ORGANISM: adeno-associated virus 2
<220> FEATURE:
<221> NAME/KEY: misc_feature
<223> OTHER INFORMATION: AT optimized

<400> SEQUENCE: 3
atggaattag taggatggtt agtagataaa ggaataacat cagaaaaaca atggatacaa    60
gaagatcaag catcatatat atcatttaat gcagcatcaa attcaagatc acaaataaaa   120
gcagcattag ataatgcagg aaaaataatg tcattaacaa aaacagcacc agattattta   180
gtaggacaac aaccagtaga agatatatca tcaaatagaa tatataaaat attagaatta   240
aatggatatg atccacaata tgcagcatca gtatttttag gatgggcaac aaaaaaattt   300
ggaaaaagaa atacaatatg gttatttgga ccagcaacaa caggaaaaac aaatatagca   360
gaagcaatag cacatacagt accatttat ggatgtgtaa attggacaaa tgaaaatttt   420
ccatttaatg attgtgtaga taaatggta atatggtggg aagaaggaaa aatgacagca   480
```

-continued

| | |
|---|---|
| aaagtagtag aatcagcaaa agcaatatta ggaggatcaa agtaagagt agatcaaaaa | 540 |
| tgtaaatcat cagcacaaat agatccaaca ccagtaatag taacatcaaa tacaaatatg | 600 |
| tgtgcagtaa tagatggaaa ttcaacaaca tttgaacatc aacaaccatt acaagataga | 660 |
| atgtttaaat ttgaattaac aagaagatta gatcatgatt ttggaaaagt aacaaaacaa | 720 |
| gaagtaaaag attttttttag atgggcaaaa gatcatgtag tagaagtaga acatgaattt | 780 |
| tatgtaaaaa aaggaggagc aaaaaaaaga ccagcaccat cagatgcaga tatatcagaa | 840 |
| ccaaaaagag taagagaatc agtagcacaa ccatcaacat cagatgcaga agcatcaata | 900 |
| aattatgcag atagatatca aaataaatgt tcaagacatg taggaatgaa tttaatgtta | 960 |
| tttccatgta gacaatgtga aagaatgaat caaaattcaa atatatgttt tacacatgga | 1020 |
| caaaaagatt gtttagaatg ttttccagta tcagaatcac aaccagtatc agtagtaaaa | 1080 |
| aaagcatatc aaaaattatg ttatatacat catataatgg gaaaagtacc agatgcatgt | 1140 |
| acagcatgtg atttagtaaa tgtagattta gatgattgta tatttgaaca ataa | 1194 |

<210> SEQ ID NO 4
<211> LENGTH: 1194
<212> TYPE: DNA
<213> ORGANISM: adeno-associated virus 2
<220> FEATURE:
<221> NAME/KEY: misc_feature
<222> LOCATION: (1)..(1194)
<223> OTHER INFORMATION: GC optimized
<400> SEQUENCE: 4

| | |
|---|---|
| atggagctgg tggggtggct ggtggacaag gggatcacga gcgagaagca gtggatccag | 60 |
| gaggaccagg cgagctacat cagcttcaac gcggcgagca acagccggag ccagatcaag | 120 |
| gcggcgctgg acaacgcggg gaagatcatg agcctgacga gacggcgcc ggactacctg | 180 |
| gtggggcagc agccggtgga ggacatcagc agcaaccgga tctacaagat cctggagctg | 240 |
| aacgggtacg acccgcagta cgcggcgagc gtgttcctgg ggtgggcgac gaagaagttc | 300 |
| ggaagcgga acacgatctg gctgttcggg ccggcgacga cggggaagac gaacatcgcg | 360 |
| gaggcgatcg cgcacacggt gccgttctac ggtgcgtga actggacgaa cgagaacttc | 420 |
| ccgttcaacg actgcgtgga caagatggtg atctggtggg aggaggggaa gatgacggcg | 480 |
| aaggtggtgg agagcgcgaa ggcgatcctg gggggagca aggtgcgggt ggaccagaag | 540 |
| tgcaagagca gcgcgcagat cgacccgacg ccggtgatcg tgacgagcaa cacgaacatg | 600 |
| tgcgcggtga tcgacgggaa cagcacgacg ttcgagcacc agcagccgct gcaggaccgg | 660 |
| atgttcaagt tcgagctgac gcggcggctg gaccacgact tcgggaaggt gacgaagcag | 720 |
| gaggtgaagg acttcttccg gtgggcgaag gaccacgtgg tggaggtgga gcacgagttc | 780 |
| tacgtgaaga aggggggggc gaagaagcgg ccggcgccga gcgacgcgga tcatcagcgag | 840 |
| ccgaagcggg tgcgggagag cgtggcgcag ccgagcacga gcgacgcgga ggcgagcatc | 900 |
| aactacgcgg accggtacca gaacaagtgc agccggcacg tggggatgaa cctgatgctg | 960 |
| ttcccgtgcc ggcagtgcga gcggatgaac cagaacagca acatctgctt cacgcacggg | 1020 |
| cagaaggact gcctggagtg cttcccggtg agcgagagcc agccggtgag cgtggtgaag | 1080 |
| aaggcgtacc agaagctgtg ctacatccac cacatcatgg ggaaggtgcc ggacgcgtgc | 1140 |
| acggcgtgcg acctggtgaa cgtggacctg gacgactgca tcttcgagca gtaa | 1194 |

<210> SEQ ID NO 5
<211> LENGTH: 1194
<212> TYPE: DNA

<213> ORGANISM: adeno-associated virus 2
<220> FEATURE:
<221> NAME/KEY: CDS
<222> LOCATION: (1)..(1194)
<223> OTHER INFORMATION: Rep52

<400> SEQUENCE: 5

```
atg gag ctg gtc ggg tgg ctc gtg gac aag ggg att acc tcg gag aag        48
Met Glu Leu Val Gly Trp Leu Val Asp Lys Gly Ile Thr Ser Glu Lys
1               5                   10                  15 cag tgg atc cag gag gac cag gcc tca tac atc tcc ttc aat gcg gcc        96
Gln Trp Ile Gln Glu Asp Gln Ala Ser Tyr Ile Ser Phe Asn Ala Ala
            20                  25                  30 tcc aac tcg cgg tcc caa atc aag gct gcc ttg gac aat gcg gga aag       144
Ser Asn Ser Arg Ser Gln Ile Lys Ala Ala Leu Asp Asn Ala Gly Lys
        35                  40                  45 att atg agc ctg act aaa acc gcc ccc gac tac ctg gtg ggc cag cag       192
Ile Met Ser Leu Thr Lys Thr Ala Pro Asp Tyr Leu Val Gly Gln Gln
    50                  55                  60 ccc gtg gag gac att tcc agc aat cgg att tat aaa att ttg gaa cta       240
Pro Val Glu Asp Ile Ser Ser Asn Arg Ile Tyr Lys Ile Leu Glu Leu
65                  70                  75                  80 aac ggg tac gat ccc caa tat gcg gct tcc gtc ttt ctg gga tgg gcc       288
Asn Gly Tyr Asp Pro Gln Tyr Ala Ala Ser Val Phe Leu Gly Trp Ala
                85                  90                  95 acg aaa aag ttc ggc aag agg aac acc atc tgg ctg ttt ggg cct gca       336
Thr Lys Lys Phe Gly Lys Arg Asn Thr Ile Trp Leu Phe Gly Pro Ala
            100                 105                 110 act acc ggg aag acc aac atc gcg gag gcc ata gcc cac act gtg ccc       384
Thr Thr Gly Lys Thr Asn Ile Ala Glu Ala Ile Ala His Thr Val Pro
        115                 120                 125 ttc tac ggg tgc gta aac tgg acc aat gag aac ttt ccc ttc aac gac       432
Phe Tyr Gly Cys Val Asn Trp Thr Asn Glu Asn Phe Pro Phe Asn Asp
    130                 135                 140 tgt gtc gac aag atg gtg atc tgg tgg gag gag ggg aag atg acc gcc       480
Cys Val Asp Lys Met Val Ile Trp Trp Glu Glu Gly Lys Met Thr Ala
145                 150                 155                 160 aag gtc gtg gag tcg gcc aaa gcc att ctc gga gga agc aag gtg cgc       528
Lys Val Val Glu Ser Ala Lys Ala Ile Leu Gly Gly Ser Lys Val Arg
                165                 170                 175 gtg gac cag aaa tgc aag tcc tcg gcc cag ata gac ccg act ccc gtg       576
Val Asp Gln Lys Cys Lys Ser Ser Ala Gln Ile Asp Pro Thr Pro Val
            180                 185                 190 atc gtc acc tcc aac acc aac atg tgc gcc gtg att gac ggg aac tca       624
Ile Val Thr Ser Asn Thr Asn Met Cys Ala Val Ile Asp Gly Asn Ser
        195                 200                 205 acg acc ttc gaa cac cag cag ccg ttg caa gac cgg atg ttc aaa ttt       672
Thr Thr Phe Glu His Gln Gln Pro Leu Gln Asp Arg Met Phe Lys Phe
    210                 215                 220 gaa ctc acc cgc cgt ctg gat cat gac ttt ggg aag gtc acc aag cag       720
Glu Leu Thr Arg Arg Leu Asp His Asp Phe Gly Lys Val Thr Lys Gln
225                 230                 235                 240 gaa gtc aaa gac ttt ttc cgg tgg gca aag gat cac gtg gtt gag gtg       768
Glu Val Lys Asp Phe Phe Arg Trp Ala Lys Asp His Val Val Glu Val
                245                 250                 255 gag cat gaa ttc tac gtc aaa aag ggt gga gcc aag aaa aga ccc gcc       816
Glu His Glu Phe Tyr Val Lys Lys Gly Gly Ala Lys Lys Arg Pro Ala
            260                 265                 270 ccc agt gac gca gat ata agt gag ccc aaa cgg gtg cgc gag tca gtt       864
Pro Ser Asp Ala Asp Ile Ser Glu Pro Lys Arg Val Arg Glu Ser Val
        275                 280                 285
```

-continued

```
gcg cag cca tcg acg tca gac gcg gaa gct tcg atc aac tac gca gac      912
Ala Gln Pro Ser Thr Ser Asp Ala Glu Ala Ser Ile Asn Tyr Ala Asp
    290                 295                 300
cgc tac caa aac aaa tgt tct cgt cac gtg ggc atg aat ctg atg ctg      960
Arg Tyr Gln Asn Lys Cys Ser Arg His Val Gly Met Asn Leu Met Leu
305                 310                 315                 320
ttt ccc tgc aga caa tgc gag aga atg aat cag aat tca aat atc tgc     1008
Phe Pro Cys Arg Gln Cys Glu Arg Met Asn Gln Asn Ser Asn Ile Cys
                325                 330                 335
ttc act cac gga cag aaa gac tgt tta gag tgc ttt ccc gtg tca gaa     1056
Phe Thr His Gly Gln Lys Asp Cys Leu Glu Cys Phe Pro Val Ser Glu
            340                 345                 350
tct caa ccc gtt tct gtc gtc aaa aag gcg tat cag aaa ctg tgc tac     1104
Ser Gln Pro Val Ser Val Val Lys Lys Ala Tyr Gln Lys Leu Cys Tyr
        355                 360                 365
att cat cat atc atg gga aag gtg cca gac gct tgc act gcc tgc gat     1152
Ile His His Ile Met Gly Lys Val Pro Asp Ala Cys Thr Ala Cys Asp
    370                 375                 380
ctg gtc aat gtg gat ttg gat gac tgc atc ttt gaa caa taa             1194
Leu Val Asn Val Asp Leu Asp Asp Cys Ile Phe Glu Gln
385                 390                 395

<210> SEQ ID NO 6
<211> LENGTH: 397
<212> TYPE: PRT
<213> ORGANISM: adeno-associated virus 2

<400> SEQUENCE: 6

Met Glu Leu Val Gly Trp Leu Val Asp Lys Gly Ile Thr Ser Glu Lys
1               5                   10                  15

Gln Trp Ile Gln Glu Asp Gln Ala Ser Tyr Ile Ser Phe Asn Ala Ala
            20                  25                  30

Ser Asn Ser Arg Ser Gln Ile Lys Ala Ala Leu Asp Asn Ala Gly Lys
        35                  40                  45

Ile Met Ser Leu Thr Lys Thr Ala Pro Asp Tyr Leu Val Gly Gln Gln
    50                  55                  60

Pro Val Glu Asp Ile Ser Ser Asn Arg Ile Tyr Lys Ile Leu Glu Leu
65                  70                  75                  80

Asn Gly Tyr Asp Pro Gln Tyr Ala Ala Ser Val Phe Leu Gly Trp Ala
                85                  90                  95

Thr Lys Lys Phe Gly Lys Arg Asn Thr Ile Trp Leu Phe Gly Pro Ala
            100                 105                 110

Thr Thr Gly Lys Thr Asn Ile Ala Glu Ala Ile Ala His Thr Val Pro
        115                 120                 125

Phe Tyr Gly Cys Val Asn Trp Thr Asn Glu Asn Phe Pro Phe Asn Asp
    130                 135                 140

Cys Val Asp Lys Met Val Ile Trp Trp Glu Glu Gly Lys Met Thr Ala
145                 150                 155                 160

Lys Val Val Glu Ser Ala Lys Ala Ile Leu Gly Gly Ser Lys Val Arg
                165                 170                 175

Val Asp Gln Lys Cys Lys Ser Ser Ala Gln Ile Asp Pro Thr Pro Val
            180                 185                 190

Ile Val Thr Ser Asn Thr Asn Met Cys Ala Val Ile Asp Gly Asn Ser
        195                 200                 205

Thr Thr Phe Glu His Gln Gln Pro Leu Gln Asp Arg Met Phe Lys Phe
    210                 215                 220

Glu Leu Thr Arg Arg Leu Asp His Asp Phe Gly Lys Val Thr Lys Gln
225                 230                 235                 240
```

```
Glu Val Lys Asp Phe Phe Arg Trp Ala Lys Asp His Val Val Glu Val
                245                 250                 255

Glu His Glu Phe Tyr Val Lys Lys Gly Gly Ala Lys Lys Arg Pro Ala
            260                 265                 270

Pro Ser Asp Ala Asp Ile Ser Glu Pro Lys Arg Val Arg Glu Ser Val
        275                 280                 285

Ala Gln Pro Ser Thr Ser Asp Ala Glu Ala Ser Ile Asn Tyr Ala Asp
290                 295                 300

Arg Tyr Gln Asn Lys Cys Ser Arg His Val Gly Met Asn Leu Met Leu
305                 310                 315                 320

Phe Pro Cys Arg Gln Cys Glu Arg Met Asn Gln Asn Ser Asn Ile Cys
                325                 330                 335

Phe Thr His Gly Gln Lys Asp Cys Leu Glu Cys Phe Pro Val Ser Glu
            340                 345                 350

Ser Gln Pro Val Ser Val Val Lys Lys Ala Tyr Gln Lys Leu Cys Tyr
        355                 360                 365

Ile His His Ile Met Gly Lys Val Pro Asp Ala Cys Thr Ala Cys Asp
    370                 375                 380

Leu Val Asn Val Asp Leu Asp Asp Cys Ile Phe Glu Gln
385                 390                 395

<210> SEQ ID NO 7
<211> LENGTH: 1876
<212> TYPE: DNA
<213> ORGANISM: adeno-associated virus 2
<220> FEATURE:
<221> NAME/KEY: CDS
<222> LOCATION: (11)..(1876)
<223> OTHER INFORMATION: Rep78

<400> SEQUENCE: 7
cgcagccgcc atg ccg ggg ttt tac gag att gtg att aag gtc ccc agc         49
           Met Pro Gly Phe Tyr Glu Ile Val Ile Lys Val Pro Ser
           1               5                   10 gac ctt gac gag cat ctg ccc ggc att tct gac agc ttt gtg aac tgg        97
Asp Leu Asp Glu His Leu Pro Gly Ile Ser Asp Ser Phe Val Asn Trp
        15                  20                  25 gtg gcc gag aag gaa tgg gag ttg ccg cca gat tct gac atg gat ctg       145
Val Ala Glu Lys Glu Trp Glu Leu Pro Pro Asp Ser Asp Met Asp Leu
30                  35                  40                  45 aat ctg att gag cag gca ccc ctg acc gtg gcc gag aag ctg cag cgc       193
Asn Leu Ile Glu Gln Ala Pro Leu Thr Val Ala Glu Lys Leu Gln Arg
                50                  55                  60 gac ttt ctg acg gaa tgg cgc cgt gtg agt aag gcc ccg gag gcc ctt       241
Asp Phe Leu Thr Glu Trp Arg Arg Val Ser Lys Ala Pro Glu Ala Leu
            65                  70                  75 ttc ttt gtg caa ttt gag aag gga gag agc tac ttc cac atg cac gtg       289
Phe Phe Val Gln Phe Glu Lys Gly Glu Ser Tyr Phe His Met His Val
        80                  85                  90 ctc gtg gaa acc acc ggg gtg aaa tcc atg gtt ttg gga cgt ttc ctg       337
Leu Val Glu Thr Thr Gly Val Lys Ser Met Val Leu Gly Arg Phe Leu
    95                  100                 105 agt cag att cgc gaa aaa ctg att cag aga att tac cgc ggg atc gag       385
Ser Gln Ile Arg Glu Lys Leu Ile Gln Arg Ile Tyr Arg Gly Ile Glu
110                 115                 120                 125 ccg act ttg cca aac tgg ttc gcg gtc aca aag acc aga aat ggc gcc       433
Pro Thr Leu Pro Asn Trp Phe Ala Val Thr Lys Thr Arg Asn Gly Ala
                130                 135                 140 gga ggc ggg aac aag gtg gtg gat gag tgc tac atc ccc aat tac ttg       481
```

```
               Gly Gly Gly Asn Lys Val Val Asp Glu Cys Tyr Ile Pro Asn Tyr Leu
                           145                 150                 155 ctc ccc aaa acc cag cct gag ctc cag tgg gcg tgg act aat atg gaa           529
Leu Pro Lys Thr Gln Pro Glu Leu Gln Trp Ala Trp Thr Asn Met Glu
            160                 165                 170 cag tat tta agc gcc tgt ttg aat ctc acg gag cgt aaa cgg ttg gtg           577
Gln Tyr Leu Ser Ala Cys Leu Asn Leu Thr Glu Arg Lys Arg Leu Val
        175                 180                 185 gcg cag cat ctg acg cac gtg tcg cag acg cag gag cag aac aaa gag           625
Ala Gln His Leu Thr His Val Ser Gln Thr Gln Glu Gln Asn Lys Glu
190                 195                 200                 205 aat cag aat ccc aat tct gat gcg ccg gtg atc aga tca aaa act tca           673
Asn Gln Asn Pro Asn Ser Asp Ala Pro Val Ile Arg Ser Lys Thr Ser
                210                 215                 220 gcc agg tac atg gag ctg gtc ggg tgg ctc gtg gac aag ggg att acc           721
Ala Arg Tyr Met Glu Leu Val Gly Trp Leu Val Asp Lys Gly Ile Thr
            225                 230                 235 tcg gag aag cag tgg atc cag gag gac cag gcc tca tac atc tcc ttc           769
Ser Glu Lys Gln Trp Ile Gln Glu Asp Gln Ala Ser Tyr Ile Ser Phe
        240                 245                 250 aat gcg gcc tcc aac tcg cgg tcc caa atc aag gct gcc ttg gac aat           817
Asn Ala Ala Ser Asn Ser Arg Ser Gln Ile Lys Ala Ala Leu Asp Asn
255                 260                 265 gcg gga aag att atg agc ctg act aaa acc gcc ccc gac tac ctg gtg           865
Ala Gly Lys Ile Met Ser Leu Thr Lys Thr Ala Pro Asp Tyr Leu Val
270                 275                 280                 285 ggc cag cag ccc gtg gag gac att tcc agc aat cgg att tat aaa att           913
Gly Gln Gln Pro Val Glu Asp Ile Ser Ser Asn Arg Ile Tyr Lys Ile
            290                 295                 300 ttg gaa cta aac ggg tac gat ccc caa tat gcg gct tcc gtc ttt ctg           961
Leu Glu Leu Asn Gly Tyr Asp Pro Gln Tyr Ala Ala Ser Val Phe Leu
        305                 310                 315 gga tgg gcc acg aaa aag ttc ggc aag agg aac acc atc tgg ctg ttt           1009
Gly Trp Ala Thr Lys Lys Phe Gly Lys Arg Asn Thr Ile Trp Leu Phe
        320                 325                 330 ggg cct gca act acc ggg aag acc aac atc gcg gag gcc ata gcc cac           1057
Gly Pro Ala Thr Thr Gly Lys Thr Asn Ile Ala Glu Ala Ile Ala His
        335                 340                 345 act gtg ccc ttc tac ggg tgc gta aac tgg acc aat gag aac ttt ccc           1105
Thr Val Pro Phe Tyr Gly Cys Val Asn Trp Thr Asn Glu Asn Phe Pro
350                 355                 360                 365 ttc aac gac tgt gtc gac aag atg gtg atc tgg tgg gag gag ggg aag           1153
Phe Asn Asp Cys Val Asp Lys Met Val Ile Trp Trp Glu Glu Gly Lys
            370                 375                 380 atg acc gcc aag gtc gtg gag tcg gcc aaa gcc att ctc gga gga agc           1201
Met Thr Ala Lys Val Val Glu Ser Ala Lys Ala Ile Leu Gly Gly Ser
        385                 390                 395 aag gtg cgc gtg gac cag aaa tgc aag tcc tcg gcc cag ata gac ccg           1249
Lys Val Arg Val Asp Gln Lys Cys Lys Ser Ser Ala Gln Ile Asp Pro
        400                 405                 410 act ccc gtg atc gtc acc tcc aac acc aac atg tgc gcc gtg att gac           1297
Thr Pro Val Ile Val Thr Ser Asn Thr Asn Met Cys Ala Val Ile Asp
415                 420                 425 ggg aac tca acg acc ttc gaa cac cag cag ccg ttg caa gac cgg atg           1345
Gly Asn Ser Thr Thr Phe Glu His Gln Gln Pro Leu Gln Asp Arg Met
430                 435                 440                 445 ttc aaa ttt gaa ctc acc cgc cgt ctg gat cat gac ttt ggg aag gtc           1393
Phe Lys Phe Glu Leu Thr Arg Arg Leu Asp His Asp Phe Gly Lys Val
            450                 455                 460 acc aag cag gaa gtc aaa gac ttt ttc cgg tgg gca aag gat cac gtg           1441
```

```
                Thr Lys Gln Glu Val Lys Asp Phe Phe Arg Trp Ala Lys Asp His Val
                            465                 470                 475 gtt gag gtg gag cat gaa ttc tac gtc aaa aag ggt gga gcc aag aaa       1489
Val Glu Val Glu His Glu Phe Tyr Val Lys Lys Gly Gly Ala Lys Lys
            480                 485                 490 aga ccc gcc ccc agt gac gca gat ata agt gag ccc aaa cgg gtg cgc       1537
Arg Pro Ala Pro Ser Asp Ala Asp Ile Ser Glu Pro Lys Arg Val Arg
    495                 500                 505 gag tca gtt gcg cag cca tcg acg tca gac gcg gaa gct tcg atc aac       1585
Glu Ser Val Ala Gln Pro Ser Thr Ser Asp Ala Glu Ala Ser Ile Asn
510                 515                 520                 525 tac gca gac agg tac caa aac aaa tgt tct cgt cac gtg ggc atg aat       1633
Tyr Ala Asp Arg Tyr Gln Asn Lys Cys Ser Arg His Val Gly Met Asn
                530                 535                 540 ctg atg ctg ttt ccc tgc aga caa tgc gag aga atg aat cag aat tca       1681
Leu Met Leu Phe Pro Cys Arg Gln Cys Glu Arg Met Asn Gln Asn Ser
            545                 550                 555 aat atc tgc ttc act cac gga cag aaa gac tgt tta gag tgc ttt ccc       1729
Asn Ile Cys Phe Thr His Gly Gln Lys Asp Cys Leu Glu Cys Phe Pro
        560                 565                 570 gtg tca gaa tct caa ccc gtt tct gtc gtc aaa aag gcg tat cag aaa       1777
Val Ser Glu Ser Gln Pro Val Ser Val Val Lys Lys Ala Tyr Gln Lys
575                 580                 585 ctg tgc tac att cat cat atc atg gga aag gtg cca gac gct tgc act       1825
Leu Cys Tyr Ile His His Ile Met Gly Lys Val Pro Asp Ala Cys Thr
            590                 595                 600                 605 gcc tgc gat ctg gtc aat gtg gat ttg gat gac tgc atc ttt gaa caa       1873
Ala Cys Asp Leu Val Asn Val Asp Leu Asp Asp Cys Ile Phe Glu Gln
                610                 615                 620 taa                                                                    1876

<210> SEQ ID NO 8
<211> LENGTH: 621
<212> TYPE: PRT
<213> ORGANISM: adeno-associated virus 2

<400> SEQUENCE: 8

Met Pro Gly Phe Tyr Glu Ile Val Ile Lys Val Pro Ser Asp Leu Asp
1               5                   10                  15

Glu His Leu Pro Gly Ile Ser Asp Ser Phe Val Asn Trp Val Ala Glu
            20                  25                  30

Lys Glu Trp Glu Leu Pro Pro Asp Ser Asp Met Asp Leu Asn Leu Ile
        35                  40                  45

Glu Gln Ala Pro Leu Thr Val Ala Glu Lys Leu Gln Arg Asp Phe Leu
    50                  55                  60

Thr Glu Trp Arg Arg Val Ser Lys Ala Pro Glu Ala Leu Phe Phe Val
65                  70                  75                  80

Gln Phe Glu Lys Gly Glu Ser Tyr Phe His Met His Val Leu Val Glu
                85                  90                  95

Thr Thr Gly Val Lys Ser Met Val Leu Gly Arg Phe Leu Ser Gln Ile
            100                 105                 110

Arg Glu Lys Leu Ile Gln Arg Ile Tyr Arg Gly Ile Glu Pro Thr Leu
        115                 120                 125

Pro Asn Trp Phe Ala Val Thr Lys Thr Arg Asn Gly Ala Gly Gly Gly
    130                 135                 140

Asn Lys Val Val Asp Glu Cys Tyr Ile Pro Asn Tyr Leu Leu Pro Lys
145                 150                 155                 160

Thr Gln Pro Glu Leu Gln Trp Ala Trp Thr Asn Met Glu Gln Tyr Leu
```

-continued

```
                165                 170                 175
Ser Ala Cys Leu Asn Leu Thr Glu Arg Lys Arg Leu Val Ala Gln His
            180                 185                 190

Leu Thr His Val Ser Gln Thr Gln Glu Gln Asn Lys Glu Asn Gln Asn
            195                 200                 205

Pro Asn Ser Asp Ala Pro Val Ile Arg Ser Lys Thr Ser Ala Arg Tyr
            210                 215                 220

Met Glu Leu Val Gly Trp Leu Val Asp Lys Gly Ile Thr Ser Glu Lys
225                 230                 235                 240

Gln Trp Ile Gln Glu Asp Gln Ala Ser Tyr Ile Ser Phe Asn Ala Ala
                245                 250                 255

Ser Asn Ser Arg Ser Gln Ile Lys Ala Ala Leu Asp Asn Ala Gly Lys
            260                 265                 270

Ile Met Ser Leu Thr Lys Thr Ala Pro Asp Tyr Leu Val Gly Gln Gln
            275                 280                 285

Pro Val Glu Asp Ile Ser Ser Asn Arg Ile Tyr Lys Ile Leu Glu Leu
            290                 295                 300

Asn Gly Tyr Asp Pro Gln Tyr Ala Ala Ser Val Phe Leu Gly Trp Ala
305                 310                 315                 320

Thr Lys Lys Phe Gly Lys Arg Asn Thr Ile Trp Leu Phe Gly Pro Ala
                325                 330                 335

Thr Thr Gly Lys Thr Asn Ile Ala Glu Ala Ile Ala His Thr Val Pro
            340                 345                 350

Phe Tyr Gly Cys Val Asn Trp Thr Asn Glu Asn Phe Pro Phe Asn Asp
            355                 360                 365

Cys Val Asp Lys Met Val Ile Trp Trp Glu Glu Gly Lys Met Thr Ala
            370                 375                 380

Lys Val Val Glu Ser Ala Lys Ala Ile Leu Gly Gly Ser Lys Val Arg
385                 390                 395                 400

Val Asp Gln Lys Cys Lys Ser Ser Ala Gln Ile Asp Pro Thr Pro Val
                405                 410                 415

Ile Val Thr Ser Asn Thr Asn Met Cys Ala Val Ile Asp Gly Asn Ser
            420                 425                 430

Thr Thr Phe Glu His Gln Gln Pro Leu Gln Asp Arg Met Phe Lys Phe
            435                 440                 445

Glu Leu Thr Arg Arg Leu Asp His Asp Phe Gly Lys Val Thr Lys Gln
            450                 455                 460

Glu Val Lys Asp Phe Phe Arg Trp Ala Lys Asp His Val Val Glu Val
465                 470                 475                 480

Glu His Glu Phe Tyr Val Lys Lys Gly Gly Ala Lys Lys Arg Pro Ala
                485                 490                 495

Pro Ser Asp Ala Asp Ile Ser Glu Pro Lys Arg Val Arg Glu Ser Val
            500                 505                 510

Ala Gln Pro Ser Thr Ser Asp Ala Glu Ala Ser Ile Asn Tyr Ala Asp
            515                 520                 525

Arg Tyr Gln Asn Lys Cys Ser Arg His Val Gly Met Asn Leu Met Leu
            530                 535                 540

Phe Pro Cys Arg Gln Cys Glu Arg Met Asn Gln Asn Ser Asn Ile Cys
545                 550                 555                 560

Phe Thr His Gly Gln Lys Asp Cys Leu Glu Cys Phe Pro Val Ser Glu
                565                 570                 575

Ser Gln Pro Val Ser Val Val Lys Ala Tyr Gln Lys Leu Cys Tyr
            580                 585                 590
```

```
Ile His His Ile Met Gly Lys Val Pro Asp Ala Cys Thr Ala Cys Asp
        595                 600                 605

Leu Val Asn Val Asp Leu Asp Asp Cys Ile Phe Glu Gln
        610                 615                 620

<210> SEQ ID NO 9
<211> LENGTH: 9
<212> TYPE: DNA
<213> ORGANISM: adeno-associated virus 2

<400> SEQUENCE: 9 cctgttaag                                                             9

<210> SEQ ID NO 10
<211> LENGTH: 1194
<212> TYPE: DNA
<213> ORGANISM: adeno-associated virus 2
<220> FEATURE:
<221> NAME/KEY: misc_feature
<223> OTHER INFORMATION: AcMNPV optimized Rep 52 coding sequence

<400> SEQUENCE: 10
atggaattgg tcggttggtt ggtggacaag ggtattacct cggagaagca atggatacaa      60
gaagatcaag cctcatacat ctcgtttaat gcggcatcca actcgcgtag ccaaatcaaa     120
gctgccttgg acaatgcggg caagattatg agcctgacta aaaccgcccc cgactacctg     180
gtgggccagc aacccgtgga agacatttcc agcaatcgca tctataagat tttggagtta     240
aacggctacg atcctcaata tgcggcttcc gtattttggg ctgggcgac gaaaaagttt      300 ggcaaaagaa acaccatttg gttgtttgga cctgcaacta cgggaaaaac aaacatagcg     360
gaggccatag cccacactgt accttttat ggctgcgtta actggaccaa tgagaacttt     420
ccattcaacg actgtgtcga caagatggtt atttggtggg aggaaggcaa aatgaccgct     480
aaagtcgtgg agtcggccaa agcaattta ggaggcagca agtgcgcgt agaccagaaa      540 tgcaaaagct ctgcgcagat agacccgaca ccggtgatcg ttacaagcaa cacgaacatg     600
tgcgccgtga ttgacggtaa cagtacgaca ttcgaacacc aacaaccgtt gcaagaccga     660
atgttcaaat ttgaattgac gcgccgactg gatcatgatt ttggcaaggt aacaaaacaa     720
gaagtcaaag acttctttcg ttgggcaaag gatcacgttg ttgaagtgga acatgaatt     780 tacgtcaaaa aggtggtgc taagaaaaga cccgccccga gtgatgcaga tataagtgag      840
cccaaacgag tgagagaatc ggttgcgcag ccaagcacgt cagatgcgga agcttcgata     900
aactacgcag accgctacca aaacaaatgt tctcgtcacg taggcatgaa cttaatgttg     960
tttccctgca gacaatgtga gagaatgaat cagaatagta atatctgttt cactcacggc    1020
cagaaagact gtttagaatg ctttccggtg tcagaatctc aacccgtttc tgtcgtaaaa    1080
aaggcgtatc aaaaattatg ctatattcat catatcatgg gaaaagtgcc agacgcttgt    1140
actgcctgcg atctggttaa tgtggatttg gatgactgta tctttgaaca ataa          1194

<210> SEQ ID NO 11
<211> LENGTH: 1866
<212> TYPE: DNA
<213> ORGANISM: Artificial
<220> FEATURE:
<223> OTHER INFORMATION: pVD189 Rep coding sequence

<400> SEQUENCE: 11
ctggcggggt ttacgagat tgtgattaag gtccccagcg accttgacga gcatctgccc       60
ggcatttctg acagctttgt gaactgggtg gccgagaagg agtgggagtt gccgccagat     120
```

```
tctgacttgg atctgaatct gattgagcag gcacccctga ccgtggccga gaagctgcag    180
cgcgactttc tgacggagtg gcgccgtgtg agtaaggccc cggaggccct tttctttgtg    240
caatttgaga agggagagag ctacttccac ttacacgtgc tcgtggaaac caccggggtg    300
aaatccttag ttttgggacg tttcctgagt cagattcgcg aaaaactgat tcagagaatt    360
taccgcggga tcgagccgac tttgccaaac tggttcgcgg tcacaaagac cagaaacggc    420
gccggaggcg ggaacaaggt ggtggacgag tgctacatcc ccaattactt gctccccaaa    480
acccagcctg agctccagtg ggcgtggact aatttagaac agtatttaag cgcctgtttg    540
aatctcacgg agcgtaaacg gttggtggcg cagcatctga cgcacgtgtc gcagacgcag    600
gagcagaaca aagagaatca gaatcccaat tctgacgcgc cggtgatcag atcaaaaact    660
tcagccaggt acatggagct ggtcggtgg ctcgtggaca aggggattac ctcggagaag    720
cagtggatcc aggaggacca ggcctcatac atctccttca atgcggcctc caactcgcgg    780
tcccaaatca aggctgcctt ggacaatgcg ggaaagatta tgagcctgac taaaaccgcc    840
cccgactacc tggtgggcca gcagcccgtg gaggacattt ccagcaatcg gatttataaa    900
attttggaac taaacgggta cgatccccaa tatgcggctt ccgtctttct gggatgggcc    960
acgaaaaagt tcggcaagag gaacaccatc tggctgtttg ggcctgcaac taccgggaag   1020
accaacatcg cggaggccat agcccacact gtgcccttct acgggtgcgt aaactggacc   1080
aatgagaact ttccccttcaa cgactgtgtc gacaagatgg tgatctggtg ggaggagggg   1140
aagatgaccg ccaaggtcgt ggagtcggcc aaagccattc tcggaggaag caaggtgcgc   1200
gtggaccaga aatgcaagtc ctcggcccag atagacccga ctcccgtgat cgtcacctcc   1260
aacaccaaca tgtgcgccgt gattgacggg aactcaacga ccttcgaaca ccagcagccg   1320
ttgcaagacc ggatgttcaa atttgaactc acccgccgtc tggatcatga ctttgggaag   1380
gtcaccaagc aggaagtcaa agactttttc cggtgggcaa aggatcacgt ggttgaggtg   1440
gagcatgaat tctacgtcaa aaagggtgga gccaagaaaa gacccgcccc cagtgacgca   1500
gatataagtg agcccaaacg ggtgcgcgag tcagttgcgc agccatcgac gtcagacgcg   1560
gaagcttcga tcaactacgc agacaggtac caaaacaaat gttctcgtca cgtgggcatg   1620
aatctgatgc tgtttcctg cagacaatgc gagagaatga atcagaattc aaatatctgc   1680
ttcactcacg gacagaaaga ctgtttagag tgctttcccg tgtcagaatc tcaacccgtt   1740
tctgtcgtca aaaaggcgta tcagaaactg tgctacattc atcatatcat gggaaaggtg   1800
ccagacgctt gcactgcctg cgatctggtc aatgtggatt tggatgactg catctttgaa   1860
caataa                                                              1866
```

BACULOVIRAL VECTORS COMPRISING REPEATED CODING SEQUENCES WITH DIFFERENTIAL CODON BIASES

FIELD OF THE INVENTION

The present invention relates to the fields of medicine, molecular biology, and gene therapy. The invention relates to production of proteins in insect cells whereby repeated coding sequences are used in baculoviral vectors. In particular the invention relates to the production of parvoviral vectors that may be used in gene therapy and to improvements in expression of the viral rep proteins that increase the productivity of parvoviral vectors.

BACKGROUND OF THE INVENTION

The baculovirus expression system is well known for its use as eukaryotic cloning and expression vector (King, L. A., and R. D. Possee, 1992, "The baculovirus expression system", Chapman and Hall, United Kingdom; O'Reilly, D. R., et al., 1992. Baculovirus Expression Vectors: A Laboratory Manual. New York: W.H. Freeman.). Advantages of the baculovirus expression system are among others that the expressed proteins are almost always soluble, correctly folded and biologically active. Further advantages include high protein expression levels, faster production, suitability for expression of large proteins and suitability for large-scale production. However, in large-scale or continuous production of heterologous proteins using the baculovirus expression system in insect cell bioreactors, the instability of production levels, also known as the passage effect, is a major obstacle. This effect is at least in part due to recombination between repeated homologous sequences in the baculoviral DNA.

The baculovirus expression system has also successfully been used for the production of recombinant Adeno-associated virus (AAV) vectors (Urabe et al., 2002, Hum. Gene Ther. 13: 1935-1943; U.S. Pat. No. 6,723,551 and US 20040197895). AAV may be considered as one of the most promising viral vectors for human gene therapy. AAV has the ability to efficiently infect dividing as well as non-dividing human cells, the AAV viral genome integrates into a single chromosomal site in the host cell's genome, and most importantly, even though AAV is present in many humans it has never been associated with any disease. In view of these advantages, recombinant adeno-associated virus (rAAV) is being evaluated in gene therapy clinical trials for hemophilia B, malignant melanoma, cystic fibrosis, hyperlipoproteinemia type I and other diseases.

To overcome problems with mammalian productions systems for AAV Urabe et al. (2002, supra) developed an AAV production system in insect cells. For production of AAV in insect cells some modifications were necessary in order to achieve the correct stoichiometry of the three AAV capsid proteins (VP1, VP2 and VP3), which relies on a combination of alternate usage of two splice acceptor sites and the suboptimal utilization of an ACG initiation codon for VP2 that is not accurately reproduced by insect cells. To mimic the correct stoichiometry of the capsid proteins in insect cells Urabe et al. (2002, supra) use a construct that is transcribed into a single polycistronic messenger that is able to express all three VP proteins without requiring splicing and wherein the most upstream initiator codon is replaced by the suboptimal initiator codon ACG. WO2007/046703 discloses further improvement of the infectivity of baculovirus-produced rAAV vectors based production by optimisation of the stoichiometry of AAV capsid proteins as produced in insect cells.

For expression of the AAV Rep proteins in the AAV insect cell expression system as initially developed by Urabe et al. (2002, supra), a recombinant baculovirus construct is used that harbours two independent Rep expression units (one for Rep78 and one for Rep52), each under the control of a separate insect cell promoter, the ΔIE1 and PolH promoters, respectively.

However, Kohlbrenner et al. (2005, Mol. Ther. 12: 1217-25; WO 2005/072364) reported that the baculovirus construct for expression of the two Rep protein, as used by Urabe et al., suffers from an inherent instability. By splitting the palindromic orientation of the two Rep genes in Urabe's original vector and designing two separate baculovirus vectors for expressing Rep52 and Rep78, Kohlbrenner et al. (2005, supra) increased the passaging stability of the vector. However, despite the consistent expression of Rep78 and Rep52 from the two independent baculovirus-Rep constructs in insect cells over at least 5 passages, rAAV vector yield is 5 to 10-fold lower as compared to the original baculovirus-Rep construct designed by Urabe et al. (2002, supra).

In WO2007/148971 the present inventors have significantly improved the stability of rAAV vector production in insect cells by using a single coding sequence for the Rep78 and Rep52 proteins wherein a suboptimal initiator codon is used for the Rep78 protein that is partially skipped by the scanning ribosomes to allow for initiation of translation to also occur further downstream at the initiation codon of the Rep52 protein.

There is however still a need for further improvements in large scale (commercial) production of heterologous proteins, including rAAV vectors, in insect cells. Thus it is an object of the present invention to provide for means and methods that allow for stable and high yield (large scale) production of heterologous proteins and parvoviral vectors.

DESCRIPTION OF THE INVENTION

Definitions

As used herein, the term "operably linked" refers to a linkage of polynucleotide (or polypeptide) elements in a functional relationship. A nucleic acid is "operably linked" when it is placed into a functional relationship with another nucleic acid sequence. For instance, a transcription regulatory sequence is operably linked to a coding sequence if it affects the transcription of the coding sequence. Operably linked means, that the DNA sequences being linked are typically contiguous and, where necessary to join two protein encoding regions, contiguous and in reading frame.

"Expression control sequence" refers to a nucleic acid sequence that regulates the expression of a nucleotide sequence to which it is operably linked. An expression control sequence is "operably linked" to a nucleotide sequence when the expression control sequence controls and regulates the transcription and/or the translation of the nucleotide sequence. Thus, an expression control sequence can include promoters, enhancers, internal ribosome entry sites (IRES), transcription terminators, a start codon in front of a protein-encoding gene, splicing signal for introns, and stop codons. The term "expression control sequence" is intended to include, at a minimum, a sequence whose presence are designed to influence expression, and can also include additional advantageous components. For example, leader sequences and fusion partner sequences are expression control sequences. The term can also include the design of the nucleic acid sequence such that undesirable, potential initiation codons in and out of frame, are removed from the sequence. It can also include the design of the nucleic acid sequence such that undesirable potential splice sites are removed. It includes sequences or polyadenylation sequences (pA) which direct the addition of a polyA tail, i.e., a string of adenine residues at the 3'-end of a mRNA, sequences referred to as polyA sequences. It also can be designed to enhance mRNA stability. Expression control sequences which affect the transcription and translation stability, e.g., promoters, as well as sequences which effect the translation, e.g., Kozak sequences, are known in insect cells. Expression control sequences can be of such nature as to modulate the nucleotide sequence to which it is operably linked such that lower expression levels or higher expression levels are achieved.

As used herein, the term "promoter" or "transcription regulatory sequence" refers to a nucleic acid fragment that functions to control the transcription of one or more coding sequences, and is located upstream with respect to the direction of transcription of the transcription initiation site of the coding sequence, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skill in the art to act directly or indirectly to regulate the amount of transcription from the promoter. A "constitutive" promoter is a promoter that is active in most tissues under most physiological and developmental conditions. An "inducible" promoter is a promoter that is physiologically or developmentally regulated, e.g. by the application of a chemical inducer. A "tissue specific" promoter is only active in specific types of tissues or cells.

The terms "substantially identical", "substantial identity" or "essentially similar" or "essential similarity" means that two peptide or two nucleotide sequences, when optimally aligned, such as by the programs GAP or BESTFIT using default parameters, share at least a certain percentage of sequence identity as defined elsewhere herein. GAP uses the Needleman and Wunsch global alignment algorithm to align two sequences over their entire length, maximizing the number of matches and minimizes the number of gaps. Generally, the GAP default parameters are used, with a gap creation penalty=50 (nucleotides)/8 (proteins) and gap extension penalty=3 (nucleotides)/2 (proteins). For nucleotides the default scoring matrix used is nwsgapdna and for proteins the default scoring matrix is Blosum62 (Henikoff & Henikoff, 1992, PNAS 89, 915-919). It is clear than when RNA sequences are said to be essentially similar or have a certain degree of sequence identity with DNA sequences, thymine (T) in the DNA sequence is considered equal to uracil (U) in the RNA sequence. Sequence alignments and scores for percentage sequence identity may be determined using computer programs, such as the GCG Wisconsin Package, Version 10.3, available from Accelrys Inc., 9685 Scranton Road, San Diego, Calif. 92121-3752 USA or the open-source software Emboss for Windows (current version 2.7.1-07). Alternatively percent similarity or identity may be determined by searching against databases such as FASTA, BLAST, etc.

Nucleotide sequences encoding parvoviral Rep proteins of the invention may also be defined by their capability to hybridise with the nucleotide sequences of SEQ ID NO.'s 1-4, respectively, under moderate, or preferably under stringent hybridisation conditions. Stringent hybridisation conditions are herein defined as conditions that allow a nucleic acid sequence of at least about 25, preferably about 50 nucleotides, 75 or 100 and most preferably of about 200 or more nucleotides, to hybridise at a temperature of about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. Preferably, the hybridisation is performed overnight, i.e. at least for 10 hours and preferably washing is performed for at least one hour with at least two changes of the washing solution. These conditions will usually allow the specific hybridisation of sequences having about 90% or more sequence identity.

Moderate conditions are herein defined as conditions that allow a nucleic acid sequences of at least 50 nucleotides, preferably of about 200 or more nucleotides, to hybridise at a temperature of about 45° C. in a solution comprising about 1 M salt, preferably 6×SSC or any other solution having a comparable ionic strength, and washing at room temperature in a solution comprising about 1 M salt, preferably 6×SSC or any other solution having a comparable ionic strength. Preferably, the hybridisation is performed overnight, i.e. at least for 10 hours, and preferably washing is performed for at least one hour with at least two changes of the washing solution. These conditions will usually allow the specific hybridisation of sequences having up to 50% sequence identity. The person skilled in the art will be able to modify these hybridisation conditions in order to specifically identify sequences varying in identity between 50% and 90%.

DETAILED DESCRIPTION OF THE INVENTION

In some aspects the present invention relates the use of animal parvoviruses, in particular dependoviruses such as infectious human or simian AAV, and the components thereof (e.g., an animal parvovirus genome) for use as vectors for introduction and/or expression of nucleic acids in mammalian cells. In particular, the invention relates to improvements in productivity of such parvoviral vectors when produced in insect cells.

Viruses of the Parvoviridae family are small DNA animal viruses. The family Parvoviridae may be divided between two subfamilies: the Parvovirinae, which infect vertebrates, and the Densovirinae, which infect insects. Members of the subfamily Parvovirinae are herein referred to as the parvoviruses and include the genus *Dependovirus*. As may be deduced from the name of their genus, members of the *Dependovirus* are unique in that they usually require coinfection with a helper virus such as adenovirus or herpes virus for productive infection in cell culture. The genus *Dependovirus* includes AAV, which normally infects humans (e.g., serotypes 1, 2, 3A, 3B, 4, 5, and 6) or primates (e.g., serotypes 1 and 4), and related viruses that infect other warm-blooded animals (e.g., bovine, canine, equine, and ovine adeno-associated viruses). Further information on parvoviruses and other members of the Parvoviridae is described in Kenneth I. Berns, "Parvoviridae: The Viruses and Their Replication," Chapter 69 in Fields Virology (3d Ed. 1996). For convenience the present invention is further exemplified and described herein by reference to AAV. It is however understood that the invention is not limited to AAV but may equally be applied to other parvoviruses.

The genomic organization of all known AAV serotypes is very similar. The genome of AAV is a linear, single-stranded DNA molecule that is less than about 5,000 nucleotides (nt) in length. Inverted terminal repeats (ITRs) flank the unique coding nucleotide sequences for the non-structural replication (Rep) proteins and the structural (VP) proteins. The VP proteins (VP1, -2 and -3) form the capsid. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. Following wtAAV infection in mammalian cells the Rep genes (i.e. Rep78 and Rep52) are expressed from the P5 promoter and the P19 promoter, respectively and both Rep proteins have a function in the replication of the viral genome. A splicing event in the Rep ORF results in the expression of actually four Rep proteins (i.e. Rep78, Rep68, Rep52 and Rep40). However, it has been shown that the unspliced mRNA, encoding Rep78 and Rep52 proteins, in mammalian cells are sufficient for AAV vector production. Also in insect cells the Rep78 and Rep52 proteins suffice for AAV vector production.

A "recombinant parvoviral or AAV vector" (or "rAAV vector") herein refers to a vector comprising one or more polynucleotide sequences of interest, genes of interest or "transgenes" that are flanked by parvoviral or AAV inverted terminal repeat sequences (ITRs). Such rAAV vectors can be replicated and packaged into infectious viral particles when present in an insect host cell that is expressing AAV rep and cap gene products (i.e. AAV Rep and Cap proteins). When an rAAV vector is incorporated into a larger nucleic acid construct (e.g. in a chromosome or in another vector such as a plasmid or baculovirus used for cloning or transfection), then the rAAV vector is typically referred to as a "pro-vector" which can be "rescued" by replication and encapsidation in the presence of AAV packaging functions and necessary helper functions.

In a first aspect the invention relates to an insect cell. The insect cell comprises at least a first nucleotide sequence coding for a first amino acid sequence and a second nucleotide sequence coding for a second amino acid sequence. Preferably, the first and second amino acid sequences each comprise a common amino acid sequence of at least 50, 80, 100, 200, 300, 350 or 398 amino acids with at least 80, 85, 90, 95, 98, 99 or 100% amino acid identity between the first and second amino acid sequences. In contrast, the nucleotide sequences that encode the common amino acid sequences in the first and second amino acid sequences (as present in the first and second nucleotide sequences, respectively) are less than 95, 90, 89, 88.4, 85, 80, 75, 70, 65, 60, or 55% identical.

Usually the first and second amino acid sequences will be heterologous to the insect cell. Preferably at least one of the common amino acid sequences in the first and second amino acid sequences is a naturally occurring amino acid sequence. More preferably, at least one of the first and second amino acid sequences is naturally occurring amino acid sequences. Most preferably, both of the first and second amino acid sequences are naturally occurring amino acid sequences.

In a preferred embodiment, the nucleotide sequence coding for the common amino acid sequence in the first nucleotide sequence has an improved codon usage bias for the insect cell as compared to the nucleotide sequence coding for the common amino acid sequence in the second nucleotide sequence. It is understood herein that whenever reference is made to codon usage bias for an insect cell, this includes codon usage bias for a baculovirus infected insect cell, including in particular codon usage bias for an *Autographa californica* multiple nucleopolyhedrovirus (AcMNPV) infected cell. The codon usage of the first nucleotide sequence encoding the common amino acid sequence preferably is adapted or optimized to the codon usage of the insect host cell. The adaptiveness of a nucleotide sequence encoding the common amino acid sequence to the codon usage of the host cell may be expressed as codon adaptation index (CAI). Preferably the codon usage is adapted to the insect cell in which the first and second nucleotide sequence are present. Usually this will be a cell of the genus *Spodoptera*, more preferably a *Spodoptera frugiperda* cell. The codon usage is thus preferably adapted to *Spodoptera frugiperda* or to an *Autographa californica* nucleopolyhedrovirus (AcMNPV) infected cell. A codon adaptation index is herein defined as a measurement of the relative adaptiveness of the codon usage of a gene towards the codon usage of highly expressed genes. The relative adaptiveness (w) of each codon is the ratio of the usage of each codon, to that of the most abundant codon for the same amino acid. The CAI index is defined as the geometric mean of these relative adaptiveness values. Non-synonymous codons and termination codons (dependent on genetic code) are excluded. CAI values range from 0 to 1, with higher values indicating a higher proportion of the most abundant codons (see Sharp and Li, 1987, Nucleic Acids Research 15: 1281-1295; also see: Kim et al., Gene. 1997, 199:293-301; zur Megede et al., Journal of Virology, 2000, 74: 2628-2635). In a preferred insect cell the difference in CAI between the nucleotide sequence coding for the common amino acid sequence in the first and second nucleotide sequence at least 0.1, 0.2, 0.3, 0.4, 0.5, 0.6, 0.7, 0.8. Preferably, in addition the CAI of the nucleotide sequence coding for the common amino acid sequence in the first nucleotide sequence is at least 0.5, 0.6, 0.7, 0.8, 0.9 or 1.0.

A preferred nucleotide sequence coding for the common amino acid sequence in the first nucleotide sequence is a coding sequence wherein at least 50, 75, 90, 95, 98 or 99%, and preferably all of the non-common codons or less-common codons are replaced with a common codon encoding the same amino acid as outlined in Table 1 or in Table 2. A common codon is herein understood to be the most frequently used codon encoding each particular amino acid residue in highly expressed *Spodoptera frugiperda* genes as shown in Table 1 or in highly expressed genes *Autographa californica* MNPV infected cells as shown in Table 2. All codons other than common codons and less-common codons are "non-common codons". The non-common codons include the "second most frequent codons", which are understood as codons having the one but highest frequency in Table 1 or Table 2. Preferably the nucleotide sequence coding for the common amino acid sequence in the first nucleotide sequence has a continuous stretch of at least 25, 50, 100, 200 or 300 codons all of which are common codons. The coding sequence may further be adapted for improved expression in the insect host cell by methods described in WO 2004/059556, and by modifying the CpG content of the coding sequence as described in WO 2006/015789. It is understood that such further adaptations may cause that not all codons in the nucleotide sequence coding for the common amino acid sequence in the first nucleotide sequence are common codons.

In a preferred embodiment of the insect cell all codons in the nucleotide sequence coding for the common amino acid sequence in the first nucleotide sequence are common codons in accordance with (either one of) Tables 1 or 2. More preferably in such an insect cell, all codons in the nucleotide sequence coding for the common amino acid sequence in the second nucleotide sequence are second most frequent codons in accordance with (either one of) Tables 1 or 2, whereby it is understood that if in the first nucleotide sequence the common codons are in accordance with Table 1, the second most frequent codons in the second nucleotide sequence are also in accordance with Table 1, or that if in the first nucleotide sequence the common codons are in accordance with Table 2, the second most frequent codons in the second nucleotide sequence are also in accordance with Table 2.

Codon optimization may be performed on the basis of the codon usage of the *Spodoptera frugiperda* organism as may be found in a codon usage database (see e.g., World Wide Web URL kazusa.or.jp/codon/). Suitable computer programs for codon optimization are available to the skilled person (see, e.g., Jayaraj et al., 2005, *Nucl. Acids Res.* 33(9):3011-3016; and on the internet). Alternatively the optimizations can be done by hand, using the same codon usage database.

In one embodiment of the insect cell of the invention, at least 50, 60, 80, 90 or 100% of the codons in the nucleotide sequence coding for the common amino acid sequence in the second nucleotide sequence are altered compared to the corresponding codon in the first nucleotide sequence to maximise the AT- or GC-content of the second nucleotide sequence.

Thus, in a preferred embodiment of the invention, the difference in nucleotide sequence between the first and second nucleotide sequence coding for the common amino acid sequences is maximised (i.e. the nucleotide identity is minimised) by one or more of: a) changing the codon bias of the first nucleotide sequence coding for the common amino acid sequence; b) changing the codon bias of the second nucleotide sequence coding for the common amino acid sequence; c) changing the GC-content of the first nucleotide sequence coding for the common amino acid sequence; and d) changing the GC-content of the second nucleotide sequence coding for the common amino acid sequence.

A preferred embodiment of the invention of the insect cell, relates to the production of parvoviral proteins in the insect cells of the invention. In particular the parvoviral proteins are produced in the insect cells in the context of producing recombinant parvoviral vectors, more preferably recombinant animal parvoviral vectors, and most preferably recombinant AAV vectors. Therefore, in this preferred embodiment of the insect cells of the invention, the first nucleotide sequence encodes an amino acid sequence of a parvoviral Rep52 or 40 protein and the second nucleotide sequence encodes an amino acid sequence of a parvoviral Rep78 or 68 protein. It is understood however that embodiments wherein the first nucleotide sequence encodes an amino acid sequence of a parvoviral Rep78 or 68 protein and the second nucleotide sequence encodes an amino acid sequence of a parvoviral Rep52 or 40 protein are expressly included in the invention. For convenience in the embodiments we shall use the nucleotide sequence encoding a parvoviral Rep52 or 40 protein as first nucleotide sequence and the nucleotide sequence encoding a parvoviral Rep78 or 68 protein as second nucleotide sequence but the reverse of these embodiments is expressly included in the invention. The common amino acid sequence encoded by the first and second nucleotide sequences comprise or consists of the amino acid sequences from at least the second amino acid to the most C-terminal amino acid of a parvoviral Rep52 or 40 protein. Preferably the common amino acid sequences comprise or consist of the first amino acid to the most C-terminal amino acid of the parvoviral Rep52 or 40 protein. The amino acid identities between the parvoviral common amino acid sequences are as defined above for the common amino acid sequences. Preferably, in the insect cell, the parvoviral Rep proteins are adeno-associated virus (AAV) Rep proteins. More preferably, the parvoviral Rep proteins encoded in the first and second nucleotide sequences are of the same serotype.

A nucleotide sequence encoding parvoviral Rep proteins, is herein understood as a nucleotide sequence encoding the non-structural Rep proteins that are required and sufficient for parvoviral vector production in insect cells such the Rep78 or Rep68, and the Rep52 or Rep40 proteins. The animal parvovirus nucleotide sequence preferably is from a *dependovirus*, more preferably from a human or simian adeno-associated virus (AAV) and most preferably from an AAV which normally infects humans (e.g., serotypes 1, 2, 3A, 3B, 4, 5, and 6) or primates (e.g., serotypes 1 and 4). An example of a nucleotide sequence encoding animal parvoviruses Rep proteins is given in SEQ ID No. 7, which depicts a part of the AAV serotype-2 sequence genome encoding the Rep proteins. The Rep78 coding sequence comprises nucleotides 11-1876 and the Rep52 coding sequence comprises nucleotides 683-1876, also depicted separately in SEQ ID No. 1 and 5. It is understood that the exact molecular weights of the Rep78 and Rep52 proteins, as well as the exact positions of the translation initiation codons may differ between different parvoviruses. However, the skilled person will know how to identify the corresponding position in nucleotide sequence from other parvoviruses than AAV-2.

A (first) nucleotide sequence encoding a parvoviral Rep52 protein may thus also be defined as a nucleotide sequence:
a) that encodes a polypeptide comprising an amino acid sequence that has at least 50, 60, 70, 80, 88, 89, 90, 95, 97, 98, or 99% sequence identity with the amino acid sequence of SEQ ID NO. 6;
b) that has at least 50, 60, 70, 80, 81, 82, 85, 90, 95, 97, 98, or 99% sequence identity with the nucleotide sequence of any one of SEQ ID NO.'s 1-5 and 10;
c) the complementary strand of which hybridises to a nucleic acid molecule sequence of (a) or (b);
d) nucleotide sequences the sequence of which differs from the sequence of a nucleic acid molecule of (c) due to the degeneracy of the genetic code.

A (second) nucleotide sequence encoding a parvoviral Rep78 protein may thus also be defined as a nucleotide sequence:
a) that encodes a polypeptide comprising an amino acid sequence that has at least 50, 60, 70, 80, 88, 89, 90, 95, 97, 98, or 99% sequence identity with the amino acid sequence of SEQ ID NO. 8;
b) that has at least 50, 60, 70, 80, 81, 82, 85, 90, 95, 97, 98, or 99% sequence identity with the nucleotide sequence of positions 11-1876 of SEQ ID NO. 7;
c) the complementary strand of which hybridises to a nucleic acid molecule sequence of (a) or (b);
d) nucleotide sequences the sequence of which differs from the sequence of a nucleic acid molecule of (c) due to the degeneracy of the genetic code.

Preferably, the nucleotide sequence encodes animal parvoviruses Rep proteins that are required and sufficient for parvoviral vector production in insect cells.

The various modifications of the first and second coding nucleotide sequence as defined above, including e.g. the wild-type parvoviral sequences, for proper expression in insect cells is achieved by application of well-known genetic engineering techniques such as described e.g. in Sambrook and Russell (2001) "Molecular Cloning: A Laboratory Manual (3rd edition), Cold Spring Harbor Laboratory, Cold Spring Harbor Laboratory Press, New York. Various further modifications of coding regions are known to the skilled artisan which could increase yield of the encode proteins. These modifications are within the scope of the present invention.

In the insect cells of the invention the first and second nucleotide sequences are preferably part of a nucleic acid construct. The insect cell may comprise two separate nucleic acid constructs, one for each of the first and second nucleotide sequences, or the insect cell may comprise a single type of nucleic acid construct comprising both the first and second nucleotide sequences.

In a further aspect the invention relates to a nucleic acid construct comprising a first and/or a second nucleotide sequence coding for a first and a second amino acid sequence, respectively, that comprise a common amino acid sequence as defined above. Preferably first and/or a second nucleotide sequences in the construct encode parvoviral Rep proteins as defined above. Preferably, in the construct, the nucleotide sequence encoding the first and second amino acid sequences are operably linked to expression control sequences for expression in an insect cell. These expression control sequences will at least include a promoter that is active in insect cells. Techniques known to one skilled in the art for expressing foreign genes in insect host cells can be used to practice the invention. Methodology for molecular engineering and expression of polypeptides in insect cells is described, for example, in Summers and Smith. 1986. A Manual of Methods for Baculovirus Vectors and Insect Culture Procedures, Texas Agricultural Experimental Station Bull. No. 7555, College Station, Tex.; Luckow. 1991. In Prokop et al., Cloning and Expression of Heterologous Genes in Insect Cells with Baculovirus Vectors' Recombinant DNA Technology and Applications, 97-152; King, L. A. and R. D. Possee, 1992, The baculovirus expression system, Chapman and Hall, United Kingdom; O'Reilly, D. R., L. K. Miller, V. A. Luckow, 1992, Baculovirus Expression Vectors: A Laboratory Manual, New York; W.H. Freeman and Richardson, C. D., 1995, Baculovirus Expression Protocols, Methods in Molecular Biology, volume 39; U.S. Pat. No. 4,745,051; US2003148506; and WO 03/074714. Suitable promoters for transcription of the first and second nucleotide sequences of the invention include e.g. the polyhedron (PolH), p10, p35, IE-1 or ΔIE-1 promoters and further promoters described in the above references. Since it is known that in mammalian cells a less abundant expression of Rep78 as compared to Rep52 favours high vector yields (Li et al., 1997, J. Virol. 71: 5236-43; Grimm et al., 1998, Hum Gene Ther. 9, 2745-2760), preferably a weaker promoter is used for driving expression of the Rep78 or 68 protein than the promoter used for expression of the Rep52 or 40 protein. E.g. the stronger polyhedron promoter may be used for expression of the Rep52 or 40 protein, the ΔIE1 promoter, a much weaker promoter than the PolH promoter, may be chosen for driving expression of the Rep78 or 68 protein. Preferably, the choice of promoters for the Rep52 or 40 protein and Rep78 or 68 protein, respectively, is such that in an insect cell so as to produce in the insect cell a molar ratio of Rep78/68 to Rep52/40 in the range of 1:10 to 10:1, 1:5 to 5:1, or 1:3 to 3:1, preferably at about 20-40 hours post infection, more preferably at about 30-40 hours post infection, using a baculovirus expression. The molar ratio of the Rep78 and Rep52 may be determined by means of Western blotting, preferably using a monoclonal antibody that recognizes a common epitope of both Rep78/68 and Rep52/40, or using e.g. a mouse anti-Rep antibody (303.9, Progen, Germany; dilution 1:50).

Preferably the nucleic acid construct for expression of the first and second nucleotide sequences of the invention in insect cells is an insect cell-compatible vector. An "insect cell-compatible vector" or "vector" is understood to be a nucleic acid molecule capable of productive transformation or transfection of an insect or insect cell. Exemplary biological vectors include plasmids, linear nucleic acid molecules, and recombinant viruses. Any vector can be employed as long as it is insect cell-compatible. The vector may integrate into the insect cells genome but the vector may also be episomal. The presence of the vector in the insect cell need not be permanent and transient episomal vectors are also included. The vectors can be introduced by any means known, for example by chemical treatment of the cells, electroporation, or infection. In a preferred embodiment, the vector is a baculovirus, a viral vector, or a plasmid. In a more preferred embodiment, the vector is a baculovirus, i.e. the construct is a baculoviral vector. Baculoviral vectors and methods for their use are described in the above cited references on molecular engineering of insect cells.

The nucleic acid constructs of the invention may further comprise an expression control sequence comprising a nine nucleotide sequence of SEQ. ID NO: 9 or a nucleotide sequence substantially homologous to SEQ. ID NO: 9, upstream of the initiation codons of the nucleotide sequence encoding the first and/or second amino acid sequences. A sequence with substantial identity to the nucleotide sequence of SEQ. ID NO: 9 and that will help increase expression of the first and/or second amino acid sequences is e.g. a sequence which has at least 60%, 70%, 80% or 90% identity to the nine nucleotide sequence of SEQ ID NO: 9.

The insect cell may be any cell that is suitable for the production of heterologous proteins. Preferably the insect cell allows for replication of baculoviral vectors and can be maintained in culture. More preferably the insect cell also allows for replication of recombinant parvoviral vectors, including rAAV vectors. For example, the cell line used can be from *Spodoptera frugiperda*, *Drosophila* cell lines, or mosquito cell lines, e.g., *Aedes albopictus* derived cell lines. Preferred insect cells or cell lines are cells from the insect species which are susceptible to baculovirus infection, including e.g. Se301, SeIZD2109, SeUCR1, Sf9, S1900+, Sf21, BTI-TN-5B1-4, MG-1, Tn368, HzAm1, Ha2302, Hz2E5, High Five (Invitrogen, CA, USA) and expresSF+® (U.S. Pat. No. 6,103,526; Protein Sciences Corp., CT, USA).

A preferred insect cell according to the invention is an insect cell for production of recombinant parvoviral vectors. This insect cell further comprises, in addition to the above described "first" and "second" nucleotide sequences or a nucleic acid constructs the first and second nucleotide sequences:

a) a third nucleotide sequence comprising at least one parvoviral inverted terminal repeat (ITR) nucleotide sequence; and, b) a fourth nucleotide sequence comprising parvoviral Cap protein coding sequences operably linked to expression control sequences for expression in an insect cell.

In the context of the invention "at least one parvoviral ITR nucleotide sequence" is understood to mean a palindromic sequence, comprising mostly complementary, symmetrically arranged sequences also referred to as "A," "B," and "C" regions. The ITR functions as an origin of replication, a site having a "cis" role in replication, i.e., being a recognition site for trans acting replication proteins such as e.g. Rep 78 (or Rep68) which recognize the palindrome and specific sequences internal to the palindrome. One exception to the symmetry of the ITR sequence is the "D" region of the ITR. It is unique (not having a complement within one ITR). Nicking of single-stranded DNA occurs at the junction between the A and D regions. It is the region where new DNA synthesis initiates. The D region normally sits to one side of the palindrome and provides directionality to the nucleic acid replication step. An parvovirus replicating in a mammalian cell typically has two ITR sequences. It is, however, possible to engineer an ITR so that binding sites are on both strands of the A regions and D regions are located symmetrically, one on each side of the palindrome. On a double-stranded circular DNA template (e.g., a plasmid), the Rep78- or Rep68-assisted nucleic acid replication then proceeds in both directions and a single ITR suffices for parvoviral replication of a circular vector. Thus, one ITR nucleotide sequence can be used in the context of the present invention. Preferably, however, two or another even number of regular ITRs are used. Most preferably, two ITR sequences are used. A preferred parvoviral ITR is an AAV ITR. For safety reasons it may be desirable to construct a recombinant parvoviral (rAAV) vector that is unable to further propagate after initial introduction into a cell in the presence of a second AAV. Such a safety mechanism for limiting undesirable vector propagation in a recipient may be provided by using rAAV with a chimeric ITR as described in US2003148506.

The number of nucleic acid constructs employed in the insect cell for the production of the recombinant parvoviral (rAAV) vector is not limiting in the invention. For example, one, two, three, four, five, or more separate constructs can be employed to produce rAAV in insect cells in accordance with the methods of the present invention. If five constructs are employed, one construct encodes AAV VP 1, another construct encodes AAV VP2, yet another construct encodes AAV VP3, still yet another construct encodes the Rep protein as defined above and a final construct comprises at least one AAV ITR. If fewer than five constructs are used, the constructs can comprise various combinations of the at least one AAV ITR and the VP1, VP2, VP3, and the Rep protein coding sequences.

Preferably, two, three or four constructs are used. If two constructs are used, preferably the insect cell comprises: (A) a first nucleic acid construct for expression of the Rep proteins as defined above, which construct further comprises the fourth nucleotide sequences as defined in (b) above (comprising parvoviral Cap protein coding sequences operably linked to at least one expression control sequence for expression in an insect cell; see also below); and (B) a third nucleic acid construct comprising the third nucleotide sequence as defined in (a) above (comprising at least one parvoviral/AAV ITR nucleotide sequence). If three constructs are used, preferably the same configuration as used for two constructs is used except that separate constructs are used for expression of the capsid proteins and for expression of the Rep proteins. If four constructs are used, preferably the same configuration as used for three constructs is used except that separate constructs are used for expression of the Rep78/68 proteins and for expression of the Rep 52/40 proteins. The sequences on each construct can be in any order relative to each other. For example, if one construct comprises ITRs and an ORF comprising nucleotide sequences encoding VP capsid proteins, the VP ORF can be located on the construct such that, upon replication of the DNA between ITR sequences, the VP ORF is replicated or not replicated. For another example, the Rep coding sequences and/or the ORF comprising nucleotide sequences encoding VP capsid proteins can be in any order on a construct. It is understood that also the third, fourth and further nucleic acid construct(s) preferably are an insect cell-compatible vectors, preferably a baculoviral vectors as described above. Alternatively, in the insect cell of the invention, one or more of the first nucleotide sequence, third nucleotide sequence, fourth nucleotide sequence, and fifth nucleotide sequence and optional further nucleotide sequences may be stably integrated in the genome of the insect cell. One of ordinary skill in the art knows how to stably introduce a nucleotide sequence into the insect genome and how to identify a cell having such a nucleotide sequence in the genome. The incorporation into the genome may be aided by, for example, the use of a vector comprising nucleotide sequences highly homologous to regions of the insect genome. The use of specific sequences, such as transposons, is another way to introduce a nucleotide sequence into a genome.

In the invention, the fourth nucleotide sequence comprising parvoviral capsid (Cap) protein coding sequences is herein understood to comprises sequences encoding each of the three parvoviral capsid proteins, VP1, -2 and -3. The fourth nucleotide sequence comprising the capsid protein coding sequences may be present in various forms. E.g. separate coding sequences for each of the capsid proteins VP1, -2 and -3 may used, whereby each coding sequence is operably linked to expression control sequences for expression in an insect cell. More preferably, however, the fourth nucleotide sequence comprises a single open reading frame encoding all three of the animal parvoviral (AAV) VP1, VP2, and VP3 capsid proteins, wherein the initiation codon for translation of the VP1 capsid protein is a suboptimal initiation codon that is not ATG as e.g. described by Urabe et al. (2002, supra) and in WO2007/046703. The suboptimal initiation codon for the VP1 capsid protein may be selected from ACG, TTG, CTG and GTG, of which CTG and GTG are most preferred. The fourth nucleotide sequence for expression of the capsid proteins may further comprises at one or modifications as described in WO2007/046703.

Various further modifications of VP coding regions are known to the skilled artisan which could either increase yield of VP and virion or have other desired effects, such as altered tropism or reduce antigenicity of the virion. These modifications are within the scope of the present invention. Preferably the nucleotide sequence of the invention encoding the parvoviral capsid proteins is operably linked to expression control sequences for expression in an insect cell, which will at least include a promoter that is active in insect cells. Such control sequences and further techniques and materials (e.g. vectors) for expressing parvoviral capsid proteins in insect host cells are already described above for the Rep proteins.

In a preferred embodiment of the invention, the third nucleotide sequence present in the insect cells of the invention, i.e. the sequence comprising at least one parvoviral (AAV) ITR, further comprises at least one nucleotide sequence encoding a gene product of interest, whereby preferably the at least one nucleotide sequence encoding a gene product of interest becomes incorporated into the genome of a recombinant parvoviral (rAAV) vector produced in the insect cell. Preferably, at least one nucleotide sequence encoding a gene product of interest is a sequence for expression in a mammalian cell. Preferably, the third nucleotide sequence comprises two parvoviral (AAV) ITR nucleotide sequences and wherein the at least one nucleotide sequence encoding a gene product of interest is located between the two parvoviral (AAV) ITR nucleotide sequences. Preferably, the nucleotide sequence encoding a gene product of interest (for expression in the mammalian cell) will be incorporated into the recombinant parvoviral (rAAV) vector produced in the insect cell if it is located between two regular ITRs, or is located on either side of an ITR engineered with two D regions.

The third nucleotide sequence defined herein above may thus comprise a nucleotide sequence encoding at least one "gene product of interest" for expression in a mammalian cell, located such that it will be incorporated into an recombinant parvoviral (rAAV) vector replicated in the insect cell. Any nucleotide sequence can be incorporated for later expression in a mammalian cell transfected with the recombinant parvoviral (rAAV) vector produced in accordance with the present invention. The nucleotide sequence may e.g. encode a protein it may express an RNAi agent, i.e. an RNA molecule that is capable of RNA interference such as e.g. a shRNA (short hairpinRNA) or an siRNA (short interfering RNA). "siRNA" means a small interfering RNA that is a short-length double-stranded RNA that are not toxic in mammalian cells (Elbashir et al., 2001, Nature 411: 494-98; Caplen et al., 2001, Proc. Natl. Acad. Sci. USA 98: 9742-47). In a preferred embodiment, the third nucleotide sequence may comprise two nucleotide sequences and each encodes one gene product of interest for expression in a mammalian cell. Each of the two nucleotide sequences encoding a product of interest is located such that it will be incorporated into a recombinant parvoviral (rAAV) vector replicated in the insect cell.

The product of interest for expression in a mammalian cell may be a therapeutic gene product. A therapeutic gene product can be a polypeptide, or an RNA molecule (siRNA), or other gene product that, when expressed in a target cell, provides a desired therapeutic effect such as e.g. ablation of an undesired activity, e.g. the ablation of an infected cell, or the complementation of a genetic defect, e.g. causing a deficiency in an enzymatic activity. Examples of therapeutic polypeptide gene products include CFTR, Factor IX, Lipoprotein lipase (LPL, preferably LPL S447X; see WO 01/00220), Apolipoprotein A1, Uridine Diphosphate Glucuronosyltransferase (UGT), Retinitis Pigmentosa GTPase Regulator Interacting Protein (RP-GRIP), and cytokines or interleukins like e.g. IL-10, porphobilinogen deaminase (PBGD), and alanine: glyoxylate aminotransferase.

Alternatively, or in addition as a third gene product, third nucleotide sequence defined herein above may comprise a nucleotide sequence encoding a polypeptide that serve as marker proteins to assess cell transformation and expression. Suitable marker proteins for this purpose are e.g. the fluorescent protein GFP, and the selectable marker genes HSV thymidine kinase (for selection on HAT medium), bacterial hygromycin B phosphotransferase (for selection on hygromycin B), Tn5 aminoglycoside phosphotransferase (for selection on G418), and dihydrofolate reductase (DHFR) (for selection on methotrexate), CD20, the low affinity nerve growth factor gene. Sources for obtaining these marker genes and methods for their use are provided in Sambrook and Russel (2001) "Molecular Cloning: A Laboratory Manual ($3^{rd}$ edition), Cold Spring Harbor Laboratory, Cold Spring Harbor Laboratory Press, New York. Furthermore, third nucleotide sequence defined herein above may comprise a nucleotide sequence encoding a polypeptide that may serve as a fail-safe mechanism that allows to cure a subject from cells transduced with the recombinant parvoviral (rAAV) vector of the invention, if deemed necessary. Such a nucleotide sequence, often referred to as a suicide gene, encodes a protein that is capable of converting a prodrug into a toxic substance that is capable of killing the transgenic cells in which the protein is expressed. Suitable examples of such suicide genes include e.g. the *E. coli* cytosine deaminase gene or one of the thymidine kinase genes from Herpes Simplex Virus, Cytomegalovirus and Varicella-Zoster virus, in which case ganciclovir may be used as prodrug to kill the transgenic cells in the subject (see e.g. Clair et al., 1987, Antimicrob. Agents Chemother. 31: 844-849).

In another embodiment one of the gene products of interest can be an AAV protein. In particular, a Rep protein, such as Rep78 or Rep68, or a functional fragment thereof. A nucleotide sequence encoding a Rep78 and/or a Rep68, if present on the genome of a recombinant parvoviral (rAAV) vector of the invention and expressed in a mammalian cell transduced with the vector, allows for integration of the recombinant parvoviral (rAAV) vector into the genome of the transduced mammalian cell. Expression of Rep78 and/or Rep68 in an rAAV-transduced or infected mammalian cell can provide an advantage for certain uses of the recombinant parvoviral (rAAV) vector, by allowing long term or permanent expression of any other gene product of interest introduced in the cell by the vector.

In the recombinant parvoviral (rAAV) vectors of the invention the at least one nucleotide sequence(s) encoding a gene product of interest for expression in a mammalian cell, preferably is/are operably linked to at least one mammalian cell-compatible expression control sequence, e.g., a promoter. Many such promoters are known in the art (see Sambrook and Russel, 2001, supra). Constitutive promoters that are broadly expressed in many cell-types, such as the CMV promoter may be used. However, more preferred will be promoters that are inducible, tissue-specific, cell-type-specific, or cell cycle-specific. For example, for liver-specific expression a promoter may be selected from an α1-anti-trypsin (AAT) promoter, a thyroid hormone-binding globulin promoter, an albumin promoter, a LPS (thyroxine-binding globlin) promoter, an HCR-ApoCII hybrid promoter, an HCR-hAAT hybrid promoter, an AAT promoter combined with the mouse albumin gene enhancer (Ealb) element and an apolipoprotein E promoter. Other examples include the E2F promoter for tumour-selective, and, in particular, neurological cell tumour-selective expression (Parr et al., 1997, Nat. Med. 3:1145-9) or the IL-2 promoter for use in mononuclear blood cells (Hagenbaugh et al., 1997, J Exp Med; 185: 2101-10).

AAV is able to infect a number of mammalian cells. See, e.g., Tratschin et al. (1985, Mol. Cell. Biol. 5:3251-3260) and Grimm et al. (1999, Hum. Gene Ther. 10:2445-2450). However, AAV transduction of human synovial fibroblasts is significantly more efficient than in similar murine cells, Jennings et al., Arthritis Res, 3:1 (2001), and the cellular tropicity of AAV differs among serotypes. See, e.g., Davidson et al. (2000, Proc. Natl. Acad. Sci. USA, 97:3428-3432), who discuss differences among AAV2, AAV4, and AAV5 with respect to mammalian CNS cell tropism and transduction efficiency.

AAV sequences that may be used in the present invention for the production of recombinant AAV vectors in insect cells can be derived from the genome of any AAV serotype. Generally, the AAV serotypes have genomic sequences of significant homology at the amino acid and the nucleic acid levels, provide an identical set of genetic functions, produce virions which are essentially physically and functionally equivalent, and replicate and assemble by practically identical mechanisms. For the genomic sequence of the various AAV serotypes and an overview of the genomic similarities see e.g. GenBank Accession number U89790; GenBank Accession number J01901; GenBank Accession number AF043303; GenBank Accession number AF085716; Chlorini et al. (1997, J. Vir. 71: 6823-33); Srivastava et al. (1983, J. Vir. 45:555-64); Chlorini et al. (1999, J. Vir. 73:1309-1319); Rutledge et al. (1998, J. Vir. 72:309-319); and Wu et al. (2000, J. Vir. 74: 8635-47). AAV serotypes 1, 2, 3, 4 and 5 are preferred source of AAV nucleotide sequences for use in the context of the present invention. Preferably the AAV ITR sequences for use in the context of the present invention are derived from AAV1, AAV2, and/or AAV4. Likewise, the Rep (Rep78/68 and Rep52/40) coding sequences are preferably derived from AAV1, AAV2, and/or AAV4. The sequences coding for the VP1, VP2, and VP3 capsid proteins for use in the context of the present invention may however be taken from any of the known 42 serotypes, more preferably from AAV1, AAV2, AAV3, AAV4, AAV5, AAV6, AAV7, AAV8 or AAV9 or newly developed AAV-like particles obtained by e.g. capsid shuffling techniques and AAV capsid libraries.

AAV Rep and ITR sequences are particularly conserved among most serotypes. The Rep78 proteins of various AAV serotypes are e.g. more than 89% identical and the total nucleotide sequence identity at the genome level between AAV2, AAV3A, AAV3B, and AAV6 is around 82% (Bantel-Schaal et al., 1999, J. Virol., 73(2):939-947). Moreover, the Rep sequences and ITRs of many AAV serotypes are known to efficiently cross-complement (i.e., functionally substitute) corresponding sequences from other serotypes in production of AAV particles in mammalian cells. US2003148506 reports that AAV Rep and ITR sequences also efficiently cross-complement other AAV Rep and ITR sequences in insect cells.

The AAV VP proteins are known to determine the cellular tropicity of the AAV virion. The VP protein-encoding sequences are significantly less conserved than Rep proteins and genes among different AAV serotypes. The ability of Rep and ITR sequences to cross-complement corresponding sequences of other serotypes allows for the production of pseudotyped rAAV particles comprising the capsid proteins of a serotype (e.g., AAV3) and the Rep and/or ITR sequences of another AAV serotype (e.g., AAV2). Such pseudotyped rAAV particles are a part of the present invention.

Modified "AAV" sequences also can be used in the context of the present invention, e.g. for the production of rAAV vectors in insect cells. Such modified sequences e.g. include sequences having at least about 70%, at least about 75%, at least about 80%, at least about 85%, at least about 90%, at least about 95%, or more nucleotide and/or amino acid sequence identity (e.g., a sequence having about 75-99% nucleotide sequence identity) to an AAV1, AAV2, AAV3, AAV4, AAV5, AAV6, AAV7, AAV8 or AAV9 ITR, Rep, or VP can be used in place of wild-type AAV ITR, Rep, or VP sequences.

Although similar to other AAV serotypes in many respects, AAV5 differs from other human and simian AAV serotypes more than other known human and simian serotypes. In view thereof, the production of rAAV5 can differ from production of other serotypes in insect cells. Where methods of the invention are employed to produce rAAV5, it is preferred that one or more constructs comprising, collectively in the case of more than one construct, a nucleotide sequence comprising an AAV5 ITR, a nucleotide sequence comprises an AAV5 Rep coding sequence (i.e. a nucleotide sequence comprises an AAV5 Rep78). Such ITR and Rep sequences can be modified as desired to obtain efficient production of rAAV5 or pseudotyped rAAV5 vectors in insect cells. E.g., the start codon of the Rep sequences can be modified, VP splice sites can be modified or eliminated, and/or the VP1 start codon and nearby nucleotides can be modified to improve the production of rAAV5 vectors in the insect cell.

In another aspect the invention relates to a method for producing a recombinant parvoviral (rAAV) virion (comprising a recombinant parvoviral (rAAV) vector as defined above) in an insect cell. Preferably, the method comprises the steps of: (a) culturing an insect cell as defined in herein above under conditions such that recombinant parvoviral (rAAV) vector is produced; and, (b) recovery of the recombinant parvoviral (rAAV) vector. It is understood here that the recombinant parvoviral (rAAV) vector produced in the method preferably is an infectious parvoviral or AAV virion that comprise the recombinant parvoviral (rAAV) vector nucleic acids. Growing conditions for insect cells in culture, and production of heterologous products in insect cells in culture are well-known in the art and described e.g. in the above cited references on molecular engineering of insects cells (see also WO2007/046703).

Preferably the method further comprises the step of affinity-purification of the (virions comprising the) recombinant parvoviral (rAAV) vector using an anti-AAV antibody, preferably an immobilised antibody. The anti-AAV antibody preferably is a monoclonal antibody. A particularly suitable antibody is a single chain camelid antibody or a fragment thereof as e.g. obtainable from camels or llamas (see e.g. Muyldermans, 2001, Biotechnol. 74: 277-302). The antibody for affinity-purification of rAAV preferably is an antibody that specifically binds an epitope on an AAV capsid protein, whereby preferably the epitope is an epitope that is present on capsid protein of more than one AAV serotype. E.g. the antibody may be raised or selected on the basis of specific binding to AAV2 capsid but at the same time also it may also specifically bind to AAV1, AAV3 and AAV5 capsids.

In yet another aspect the invention relates a nucleic acid construct comprising a first and a second nucleotide sequence as defined herein defined above.

In a different aspect the invention relates to a method for producing a recombinant parvoviral (rAAV) virion (comprising a recombinant parvoviral (rAAV) vector as defined above) in an insect cell. Preferably, the method comprises the steps of: (a) culturing an insect cell as defined in herein above under conditions such that recombinant parvoviral (rAAV) vector is produced, wherein the insect cell comprises at least one nucleic acid construct for expression of parvoviral Rep78/68 and Rep52/40 proteins (such as e.g. a nucleic acid construct comprising the first and second nucleotide sequences as defined herein above) and further comprises a third and a fourth nucleotide sequence as herein defined above, and wherein the nucleic acid construct(s) for expression of parvoviral Rep78/68 and Rep52/40 proteins produces a Rep52/40 expression level in the insect cell that is higher than the Rep78/68 expression level on a molar basis; and, (b) recovery of the recombinant parvoviral (rAAV) vector. Preferably in the method the molar ratio of Rep52/40 to Rep78/68 protein in the insect cell is higher than 10:1, preferably at least 11:1, 15:1, 20:1, 30:1, 40:1, 50:1 or 60:1. A molar ratio of Rep52/40 to Rep78/68 protein in the insect cell higher than 10:1 advantageously results in a better ration of full virions (i.e. comprising an rAAV genome) to empty virions (see e.g. FIG. 8). However, a too high molar ratio of Rep52/40 to Rep78/68 protein may result in a lower titer of the rAAV produced as determined by number of gene copies. In one embodiment therefore the molar ratio of Rep52/40 to Rep78/68 protein is less than 100:1, 80:1, 70:1, 60:1, 50:1, 40:1, 30:1, or 20:1. The molar ratio of the Rep78/68 and Rep52/40 proteins may be determined by means of Western blotting as described in WO2007/148971, preferably using a monoclonal antibody that recognizes a common epitope of both Rep78/68 and Rep52/40, or using the antibody described in WO2007/148971. Preferably, the minimal molar ratio's of the Rep52/40 and Rep78/68 proteins as indicated above are achieved at about 20-40 hours post infection, more preferably at about 30-40 hours post infection, using a baculovirus or similar expression system.

Various means exist for increasing the relative expression level of the Rep52/40 proteins as compared to that of the Rep78/68 protein. In case that a single transcription unit for expression of both Rep78/68 and Rep52/40 proteins is used, the coding sequence of the Rep78/68 and Rep52/40 proteins may be adapted as follows to obtain a molar ratio of Rep52/40 to Rep78/68 protein in the insect cell higher than 10:1:

a) the translation initiation codon of the Rep78/68 protein may be changed into a suboptimimal initiation codon and/or suboptimal context thereof as described in WO2007/148971;

b) elimination of one or more or all (9) ATG sequences that occur between the translation starts of the Rep78/68 and Rep 52/40 genes, respectively, preferably by isocoding changes in the nucleotide sequence. This is e.g. achieved in the pVD189 Rep coding sequence described in Example 3 and in SEQ ID NO: 11;

c) optimisation of the context of the translation initiation codon of the Rep52/40 protein in accordance with the optimal initiator context of 5'-N N N N N N A U G A a/c/g N-3' for efficient translation initiation in lepidopteran cells (as described in Chang et al., 1999, Virology 259:369-383);

d) by incorporating an expression control sequence comprising a nine nucleotide sequence of SEQ. ID NO: 9 or a nucleotide sequence substantially homologous to SEQ. ID NO: 9, upstream of the initiation codons of the Rep52/40 protein;

e) improving the codon usage bias of the part of the coding sequence that codes for the Rep52/40 protein for expression in insect cells (as described above); and, f) changing the codon usage of the part of the coding sequence between the translation starts of the Rep78/68 and Rep 52/40 proteins so that it is less adapted to expression in insect cells (as described above). Combination of a) to f) are included in the invention and in a preferred a) is combined with at least one of b) to f).

Alternatively, and/or in addition a second trancription unit may be used for expression of the Rep52/40 protein. Expression of the Rep52/40 protein from this second trancription unit may be increased by one or more of a) using a stronger promoter for the Rep52/40 trancription unit as compared to the promoter for the Rep78/68 unit (see below);

b) increasing the copy number of the Rep52/40 trancription unit as compared to that of the Rep78/68 unit;

c) improving the codon usage bias of the coding sequence that codes for the Rep52/40 protein for expression in insect cells (as described above; e.g. SEQ ID NO: 2 or 10);

d) optimisation of the context of the translation initiation codon of the Rep52/40 protein in accordance with the optimal initiator context of 5'-N N N N N N A U G A a/c/g N-3' for efficient translation initiation in lepidopteran cells (as described in Chang et al., supra); and, e) by incorporating an expression control sequence comprising a nine nucleotide sequence of SEQ. ID NO: 9 or a nucleotide sequence substantially homologous to SEQ. ID NO: 9, upstream of the initiation codons of the Rep52/40 protein.

An example of a construct wherein two separate transcription units are used for expression of the Rep78/68 and Rep 52/40 proteins is the pVD183 construct as described in Examples 2 and 3 herein. The nucleic acid constructs for use in the method for producing a recombinant parvoviral virion (and that produce a Rep52/40 expression level in the insect cell that is higher than the Rep78/68 expression level on a molar basis) are a further aspect of the present invention.

It is understood herein that the recombinant parvoviral (rAAV) vector produced in the method preferably is an infectious parvoviral or AAV virion that comprise the recombinant parvoviral (rAAV) vector nucleic acids. Growing conditions for insect cells in culture, and production of heterologous products in insect cells in culture are well-known in the art and described e.g. in the above cited references on molecular engineering of insects cells (see also WO2007/046703). Preferably the method further comprises the step of affinity-purification of the (virions comprising the) recombinant parvoviral (rAAV) vector using an anti-AAV antibody as described above.

A first promoter being equally strong or stronger than a second promoter for use in the invention may be defined as follows. The strength of the promoter may be determined by the expression that is obtained under conditions that are used in the method of the invention. In a preferred embodiment, the first promoter or the second promoter is selected from the group consisting of a PolH promoter, p10 promoter, basic protein promoter, an inducible promoter or a deltaE1 promoter or a E1 promoter, or any other late or very late baculovirus gene promoter. More preferably, the first promoter is selected from the group consisting of a PolH promoter, p10 promoter or basic protein promoter and wherein the second promoter is a deltaE1 promoter or a E1 promoter, or any other early or late baculovirus gene promoter. Preferably, the first promoter in the nucleic acid construct of the invention is a p10 promoter and the second promoter is a PolH promoter or a 4×Hsp27 EcRE+minimal Hsp70 promoter. In another embodiment, the first promoter in the nucleic acid construct of the invention is a 4×Hsp27 EcRE+minimal Hsp70 promoter and the second promoter is a PolH promoter. In yet another embodiment, the first promoter in the nucleic acid construct of the invention is a PolH promoter and the second promoter is a p10, a deltaE1 or an E1 promoter. In yet another embodiment, the first promoter in the nucleic acid construct of the invention is a PolH promoter and the second promoter is a deltaE1 or an E1 promoter. In yet another embodiment, the first promoter in the nucleic acid construct of the invention is a p10 promoter and the second promoter is a deltaE1 or an E1 promoter. In yet another embodiment, the first promoter in the nucleic acid construct of the invention is a PolH promoter and the second promoter is a PolH promoter. Most preferably, the first promoter in the nucleic acid construct op the invention is a PolH promoter and the second promoter is a deltaE1 promoter.

An "enhancer element" or "enhancer" is meant to define a sequence which enhances the activity of a promoter (i.e. increases the rate of transcription of a sequence downstream of the promoter) which, as opposed to a promoter, does not possess promoter activity, and which can usually function irrespective of its location with respect to the promoter (i.e. upstream, or downstream of the promoter). Enhancer elements are well-known in the art. Non-limiting examples of enhancer elements (or parts thereof) which could be used in the present invention include baculovirus enhancers and enhancer elements found in insect cells. It is preferred that the enhancer element increases in a cell the mRNA expression of a gene, to which the promoter it is operably linked, by at least 25%, more preferably at least 50%, even more preferably at least 100%, and most preferably at least 200% as compared to the mRNA expression of the gene in the absence of the enhancer element. mRNA expression may be determined for example by quantitative RT-PCR.

Herein it is preferred to use an enhancer element to enhance the expression of parvoviral Rep protein. Thus, in a further preferred embodiment, the first expression cassette comprises at least one baculovirus enhancer element and/or at least one ecdysone responsive element. Preferably the enhancer element is selected from the group consisting of hr1, hr2, hr3, hr4 and hr5.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

EXAMPLES

1. Example 1

Figure 1:
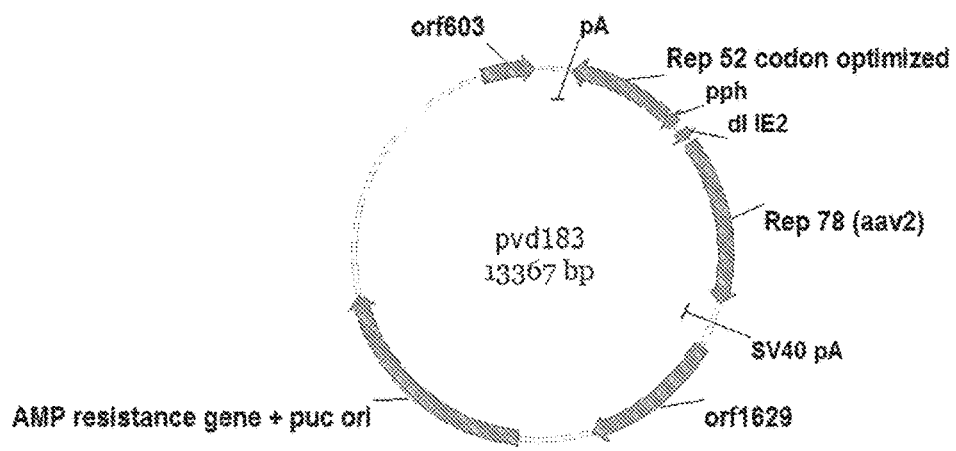
FIG. 1 Physical map of pVD183.

1.1. Materials & Methods
1.1.1 Baculovirus Plasmid Construction pFBDSLR (Urabe et al., 2002, supra) is a pFastBacDual expression vector (Invitrogen) comprising 2 separate expression cassettes for the AAV2 Rep78 and Rep52 proteins, whereby the expression of the Rep52 proteins is driven by the polH promoter and expression of the Rep78 protein from the DIE promoter. This construct has been subcloned to pPSC10, a plasmid that is compatible with the GeneXpress BaculoKIT (Protein Sciences Corporation).

The wild type Rep52 coding sequence in the Rep 52 expression cassette is replaced with the codon optimized Rep52 coding sequence of SEQ ID NO. 2 to produce pPSC10Rep-52CD.

The wild type Rep52 coding sequence in the Rep78 expression cassette of pPSC10Rep-52CD is replaced with the AT-optimized Rep52 coding sequence of SEQ ID NO. 3 to produce pPSC10Rep-52CD/78AT.

The wild type Rep52 coding sequence in the Rep78 expression cassette of pPSC10Rep-52CD is replaced with the GC-optimized Rep52 coding sequence of SEQ ID NO. 4 to produce pPSC10Rep-52CD/78GC.

1.1.2 Recombinant Baculovirus Production

Recombinant baculoviruses derived from the *Autographa californica* multiple nuclear polyhydrosis virus (AcMNPV) are produced using the GeneXpress BaculoKIT (Protein Sciences Corporation). Transfection is performed as follows: in a round bottom 14 ml tube 200 µl GRACE medium is mixed with 6 µl cellfectine (Invitrogen), and in a eppendorf tube 200 µl GRACE medium is mixed with 50 µl viral DNA (protein sciences) and 2 µg transfer plasmid (REP). The contents from the eppendorf tube are added to the tube and mixed carefully. After an incubation period of 30 minutes at RT 1,300 µl GRACE is added to the transfection mix. Insect cells in a T25 flask are washed with GRACE medium and the transfection mixture is added drop wise to the cell layer. After an incubation of 6 hours at 28° C. SF900II serum supplemented with 10% FBS is added carefully and the T25 flask was put in a 28° C. stove for 5 days after which the recombinant baculovirus is harvested.

1.2 Results

The performance of the newly designed pPSC10Rep-52CD, pPSC10Rep-52CD/78AT and pPSC10Rep-52CD/78GC pPSC10Rep is compared with the original Rep constructs pFBDSLR of Urabe et al. (2002, supra). All four constructs are serially passaged until passage 5. Recombinant AAV1 production experiments are performed using the passage 2, 3, 4, and 5 Rep-constructs in combination with a baculovirus containing an mammalian expression cassette of a reporter gene between AAV ITR's (AAV-LPL) and a baculovirus containing an insect cell expression cassette for the AAV1-Cap (AAV-cap) of respectively passage 2, 3, 4 and 5. AAV-LPL and AAV-Cap recombinant Baculovirusses as used here are described in WO2007/046703. AAV1-LPL production yields are determined by QPCR. The original baculovirus designed by Urabe et al., 2002 (original REP/Bac-to-Bac) results in a fast decrease of AAV production over 5 passages. However, the baculovirus with the REP expression units of pPSC10Rep-52CD, pPSC10Rep-52CD/78AT and pPSC10Rep-52CD/78GC results in stable AAV production over at least 5 passages. Therefore, reproducible production yields of AAV-LPL over several passages (e.g. 2 to 5) are only obtained using baculoviruses containing the pPSC10Rep-52CD, pPSC10Rep-52CD/78AT and pPSC10Rep-52CD/78GC constructs.

2. Example 2

It has previously been described that baculovirus expression vectors containing 2 separate expression cassettes for the AAV Rep78 and Rep52 proteins are genetically unstable in baculoviruses (see e.g. WO2007/148971 and Kohlbrenner et al., 2005, Mol. Ther. 12(6):1217-25). We have now set out to apply codon usage optimization (with respect to *autographa californica* multiple nucleopolyhedrovirus (AcMNPV) codon usage) of only the Rep52 coding sequence and not the Rep78 coding sequence so as to introduce sufficient changes between the previously identical parts of the Rep52 and Rep78 coding sequences to reduce the recombination events. We now show that this is indeed the case.

2.1 Cloning

A plasmid containing the original double rep expression cassettes in the Protein Sciences Corporation plasmid pPSC10, pVD42 was modified. pVD42 contains the rep78 gene driven by the deltaE1 promoter, and the rep52 gene driven by the Po1H promoter, as in the original pFBDSLR construct (Urabe et al., 2002, Hum Gene Ther. 13(16):1935-43). The rep52 coding sequence in pVD42 was replaced by a synthetic rep52 coding sequence the codon usage of which was adapted to *Autographa californica* multiple nucleopolyhedrovirus (AcMNPV) codon usage (see Table 2; and World Wide Web URL kazusa.or.jp/codon/cgi-bin/showcodon.cgi?species=46015). This AcMNPV codon optimized AAV2 rep52 coding sequence is depicted in SEQ ID NO:–10. A physical map of the resulting plasmid pVD183, comprising the AcMNPV codon optimized AAV2 rep52 coding sequence driven from the Po1H promoter and the wild type AAV2 rep78 coding sequence driven from the deltaE1 promoter, is shown in FIG. 1.

2.2 Results

We have made a recombinant baculovirus clone of the pVD183 plasmid and passaged the baculovirus 10 times to analyse its genetic stability. We analyzed the genetic stability of the construct by QPCR on the genome of the baculovirus and the Rep52 gene, by western blot, and by rAAV production efficiency of the baculovirus. At the same time the original Bac.VD42 baculovirus was passaged to passage 7 for comparison. Earlier data about the stability of the Bac.VD42 (or Bac.FBDSLR) are also mentioned in WO2007/148971 (referred to as original REP/Bac-to-Bac).

2.2.1 QPCR

Figure 2:
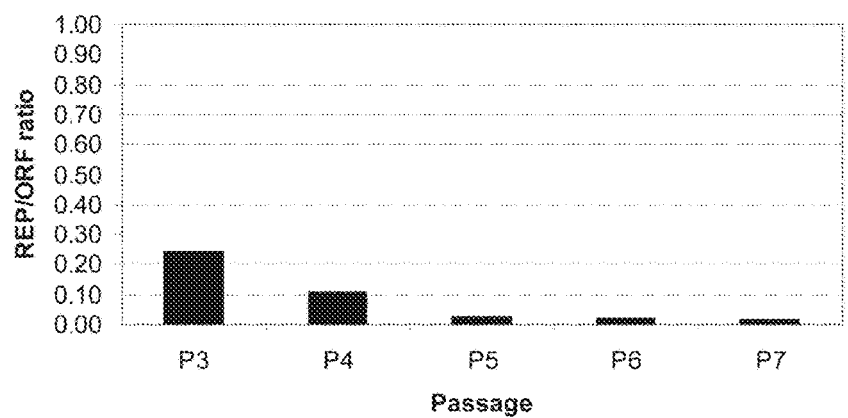
FIG. 2 Ratio's of the genomic copies of the ORF 1629 gene and the Rep gene in the baculovirus samples taken at different passages of the baculovirus Bac.FBDSLR construct (Urabe et al., 2002, Hum Gene Ther. 13(16):1935-43). Genomic copies were measured by QPCR.
Figure 3:
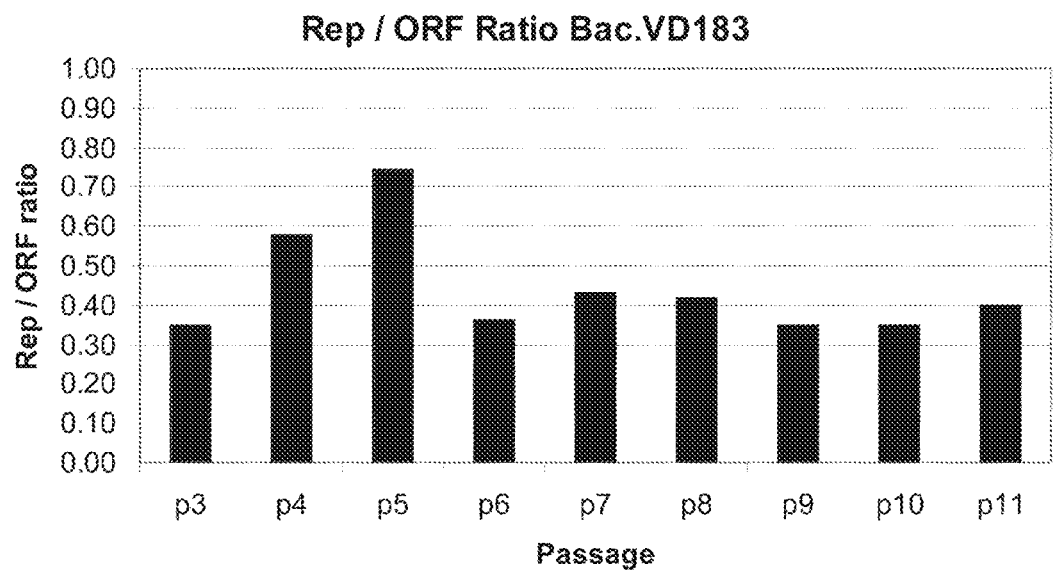
FIG. 3 Ratio's of the genomic copies of the ORF 1629 gene and the Rep gene in the baculovirus samples taken at different passages of the baculovirus pVD183 construct of the invention. Genomic copies were measured by QPCR.

Stability measured by QPCR on the baculovirus genomes. The copy number of a gene that is essential for baculovirus replication and that is used for production of the BacVD183 from pVD183 by recombination at ORF1629 and ORF603 between the pVD183 and the baculovirus backbone from Protein Sciences. ORF 1629 (ORF), has been measured by QPCR, and the copy number of the Rep genes have also been measured by QPCR. The ratio between these 2 genes should stay the same during subsequent passages of the baculovirus. FIG. 2 shows for comparison that Bac.FBDSLR is rather unstable. FIG. 3 shows that Bac.VD183 is significantly more stable. We note that the efficiency of the 2 primer sets used in the QPCR is not necessarily equal, therefore a ratio different from 1 can be obtained. A more important indicator of stability is however that the ratio should stay relatively constant during multiple passages. Passage 3 from Bac.FBDSLR is already suboptimal, as the ratio is around 0.25 and only gets worse. Bac.VD183 also starts around 0.3 but fluctuates around that ratio, indicating that there is a stable situation. Deletions in the baculovirus genome results in a baculovirus that grows faster then the baculovirus that has a full length genome, therefore when a deletion occurs, those clones will overgrow the others. Variations in the QPCR method can result in the fluctuations seen in FIG. 3.

2.2.2 rAAV Production

Figure 4:
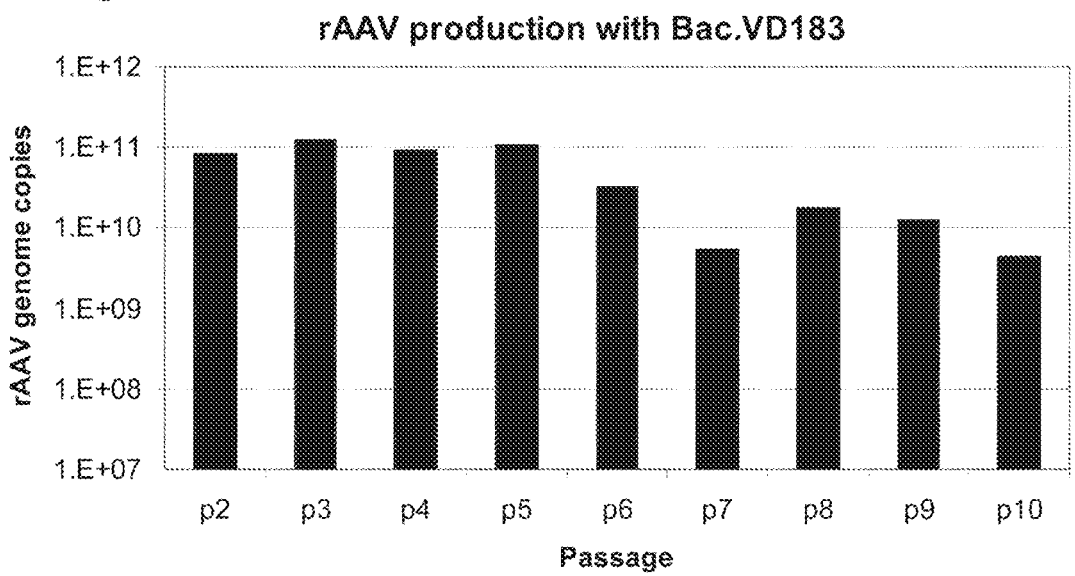
FIG. 4 rAAV production with BacVD183. The dip in the production is caused by a reduction in the amount of baculoviruses present.
Figure 5:
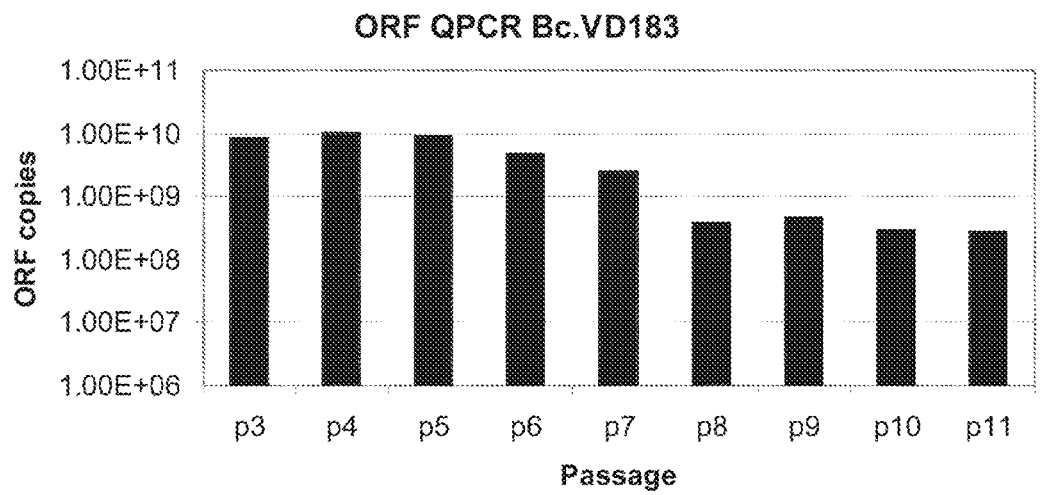
FIG. 5 ORF QPCR on the passages of Bac.VD183.

FIG. 4 shows production of rAAV with the stable Bac.VD183 construct. The dip in the production at the higher passages is caused by a reduction in the amount of baculoviruses used in the rAAV production (see FIG. 5). FIG. 5 shows the QPCR on the ORF from Bac.VD183, which is directly related to the amount of baculoviruses present in the sample. The amount of baculoviruses used in the rAAV production correlate with the amount of rAAV produced.

2.2.3 Rep Western Blot

Figure 6:
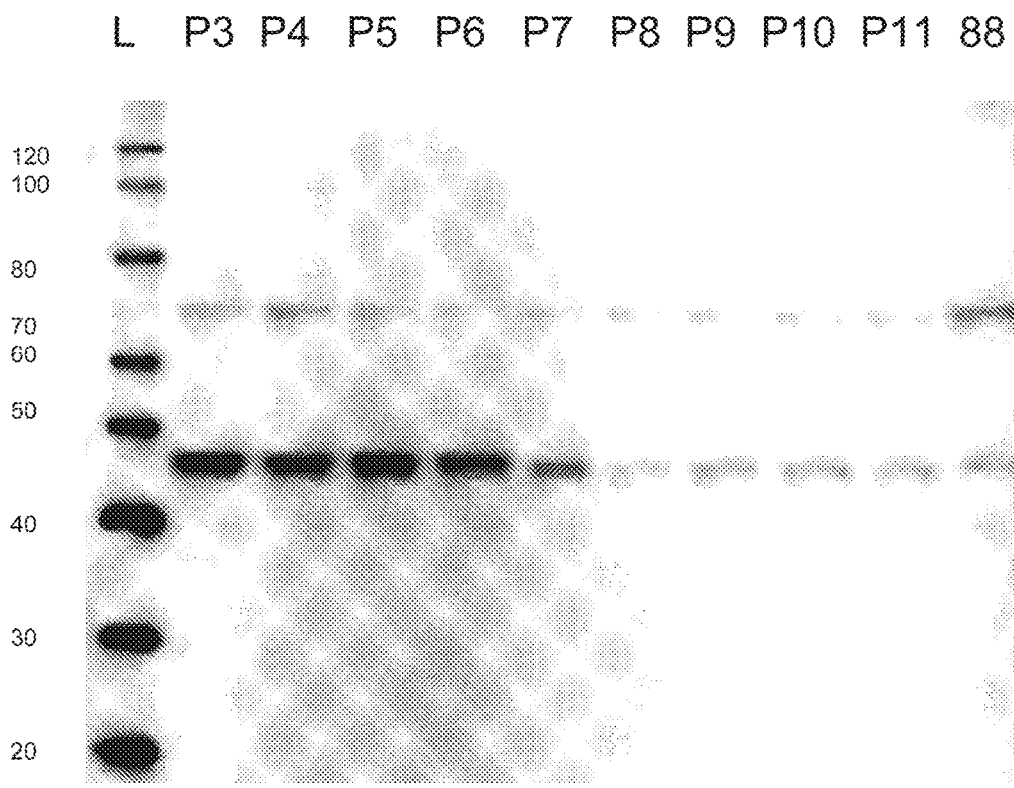
FIG. 6 Western blot Rep expression for several passages of Bac.VD183. "88" indicates the Bac.VD88 construct, which is referred to as REP-ACG/PSC in WO2007/148971, which is used here as a control. The amount of Rep expression is related to the concentration of Bac.VD183.

FIG. 6 shows rep protein expression during the passages of Bac.VD183 as analysed by Western blot.

3. Example 3

The effect of Rep52 expression level on two rAAV production parameters was determined. In particular the effect of the relative expression level Rep52 compared to the expression level of Rep78 on 1) rAAV production level as expressed in genome copies per ml crude cell bulk (gc/mL CLB); and 2) the ratio of total rAAV virions to full rAAV virions (full rAAV virions are virions comprising a rAAV genome copy). These parameters were compared for three different rAAV Rep-constructs that each result in different Rep52 expression levels and in different ratio's between Rep52 and rep78 levels. The three constructs were pVD88 (referred to as REP-ACG/PSC in WO2007/148971), pVD183 (described in Example 2 herein above), and pVD189 (see below).

3.1 Construction of pVD189

The pVD88 construct was redesigned by eliminating 9 ATG sequences between the translation start of the Rep78 and Rep 52 genes, and by changing the Rep78 ACG translation initiation codon to CTG. See the sequence below. Baseclear (Leiden, The Netherlands) synthesized the new gene and cloned it in pVD88 replacing the existing Rep gene to obtain pVD189. The nucleotide sequence of the Rep coding sequence in pVD189 is depicted in SEQ ID NO: 11.

3.2 Production of rAAV

Figure 7:
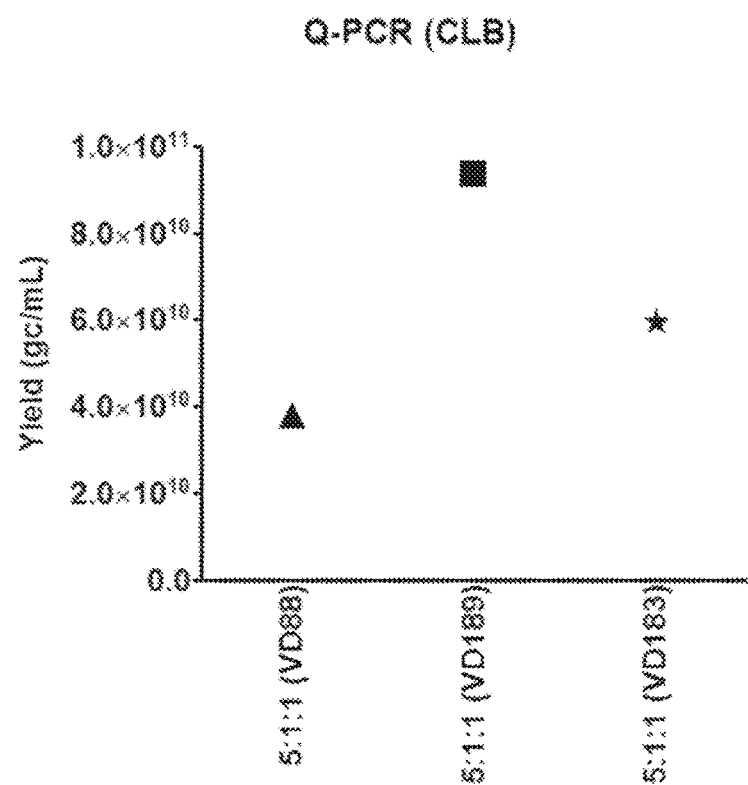
FIG. 7 Q-PCR on crude cell bulk (CLB) from rAAV1 productions using three different constructs for the Rep proteins: VD88, VD183, and VD189. 5:1:1 refers to the ration of the different baculoviruses used in the production, 5 refers to the Bac.VD88, Bac.VD183, or Bac.VD189, the first 1 refers to the Bac.VD84 (containing the AAV1 capsid gene) and the second 1 refers to the baculovirus containing the ITR construct, Bac.VD43.
Figure 9:
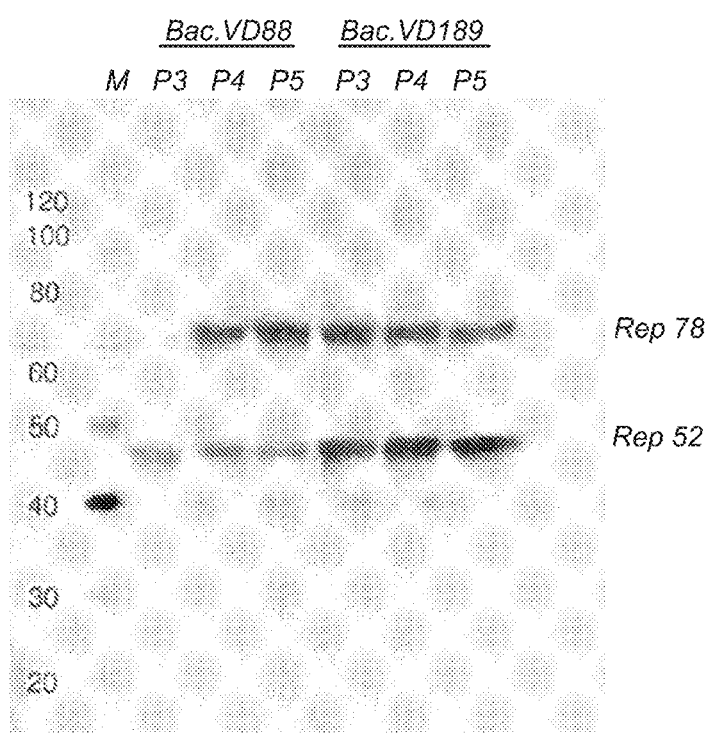
FIG. 9 Rep western blot. Samples were taken at several passages of the Bac.VD88 or Bac.VD189 baculovirus and a western blot was performed. The Rep52 amount relative to the Rep78 amount is consistently higher for Bac.VD189.
Figure 10:
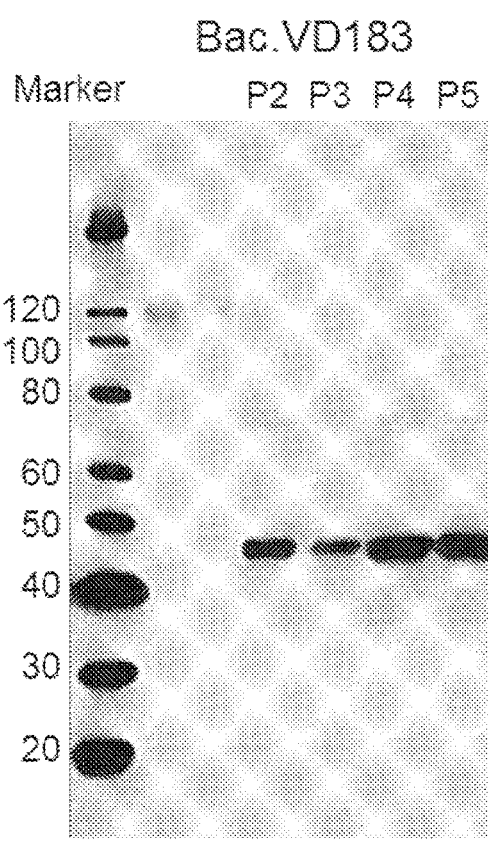
FIG. 10 Rep western blot. Samples were taken at several passages of the Bac.VD183 baculovirus amplification and a Rep western blot was performed. The Rep52 amount relative to the Rep78 amount is much higher for Bac.VD183 then for Bac.VD189 and Bac.VD88.

Baculoviruses were made with the VD88, VD183, and VD189 constructs, and these were used for production of rAAV1. Comparison of the VD88, VD183, and VD189 constructs in rAAV production resulted in better rAAV production (genome copies) as measured by Q-PCR in the crude cell bulk (CLB). FIG. 7 shows that the standard Rep construct VD88 which results in the lowest amount of Rep52 (FIG. 9) results in approximately $4 \times 10^{10}$ GC/ml measured in the CLB. VD189 which leads to a slightly higher Rep 52 amount (FIG. 9) resulted in an rAAV production measured in CLB of approximately $9.5 \times 10^{10}$ GC/ml. VD183 which leads to a clearly higher Rep52 amount (FIG. 10) and resulted a rAAV production measured in CLB of approximately $6 \times 10^{10}$ GC/ml.

Figure 8:
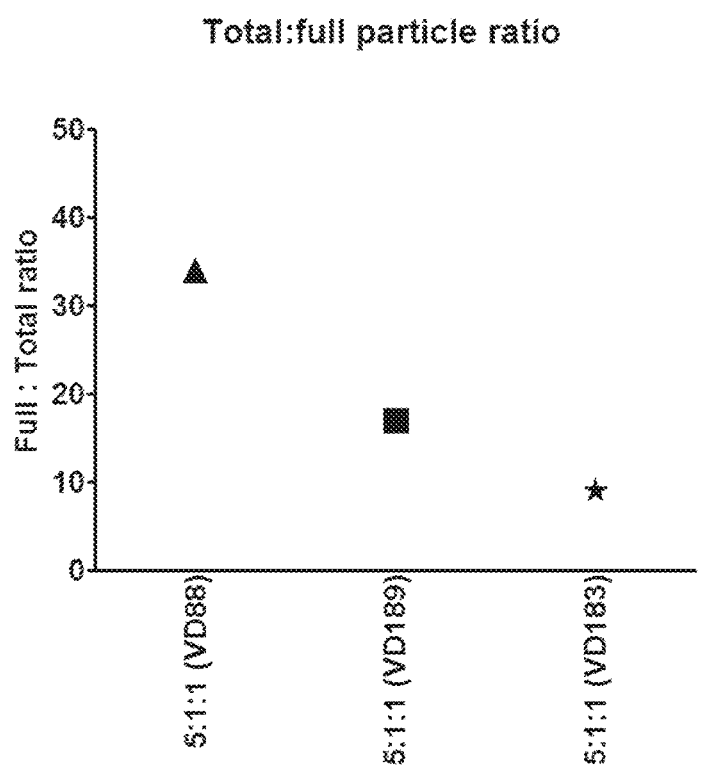
FIG. 8 The CLB's from the three different rAAV 1 production were purified in a Llama column specific for the AAV capsid and in the purified batches the genomic copies and the total rAAV particles were measured. Dividing the total rAAV particles by the Q-PCR number results in the total:full ratio mentioned here. 5:1:1 refers to the ratio of the different baculoviruses used in the production, 5 refers to the Bac.VD88, Bac.VD183, or Bac.VD189, the first 1 refers to the Bac.VD84 (containing the AAV1 capsid gene) and the second one refers to the baculovirus containing the ITR construct, Bac.VD43.

A very important quality parameter is the total:full ratio of the rAAV batch. FIG. 8 shows that the best ratio of total (virions): full (virions) is obtained with the VD183 construct that shows the highest Rep52 amount relative to the Rep78 amount as compared to the Bac.VD189 and Bac.VD88 constructs in FIG. 9.

3.2 Additional Constructs

The following constructs are constructed, tested and part of the invention:

| Constructs | promoter(s) | initation codons and coding sequences |
|---|---|---|
| 1) VD88 | PolH | ACG-78--------------ATG-52------------* |
| 2) VD189 | PolH | CTG-78-atg's removed-ATG-52------------* |

-continued

| Constructs | promoter(s) | initation codons and coding sequences | |
|---|---|---|---|
| 3) VD183 | delta E1 | ATG-78----------------------------------* | + |
| | PolH | ATG---52---SEQ ID NO: 10-----------* | |
| 4) VD196 | PolH | CTG-78---------------ATG-52------------* | |
| 5) VD197 | PolH | ACG-78-atg's removed-ATG-52------------* | |
| 6) VD197/52 | P10 | ACG-78-atg's removed-ATG-52------------* | + |
| | PolH | ATG--52---SEQ ID NO: 10-----------* | |
| 7) VD189/52 | P10 | CTG--78-atg's removed-ATG-52-----------* | + |
| | PolH | ATG--52---SEQ ID NO: 10-----------* | |
| 8) VD183/10 | p10 | ATG--78---------------------------------* | + |
| | PolH | ATG--52---SEQ ID NO: 10-----------* | |
| 9) VD197/52cd | PolH | ACG-78-atg's removed-ATG-52-SEQ ID NO: 10* | |

1, 2, 4, 5, 8, and 9 have 1 trancription unit for expression Rep 78 and 52 proteins. 3, 6, and 7 have 2 trancription units for expression Rep 78 and 52 proteins.

A rough estimate of the rep 78 and rep 52 proteins amounts and ratios for the different constructs during rAAV production (rep78:rep52):

| | 78 | 52 |
|---|---|---|
| 1) | 1 | :1 |
| 2) | 1.5 | :2 |
| 3) | 1 | :20 |
| 4) | 5 | :0.25 |
| 5) | 1 | :5 |
| 6) | 0.5 | :30 |
| 7) | 0.75 | :30 |
| 8) | 5 | :20 |
| 9) | 1 | :10 |

TABLE 1

*Spodoptera frugiperda* codon frequencies based on 127 coding sequences (33098 codons)
fields: [triplet] [frequency: per thousand] ([number])

| | | | | | | | |
|---|---|---|---|---|---|---|---|
| TTT | 9.7(320) | TCT | 10.5(347) | TAT | 10.1(334) | TGT | 6.9(227) |
| TTC | 26.9(889) | TCC | 13.0(430) | TAC | 24.4(807) | TGC | 12.4(409) |
| TTA | 7.0(233) | TCA | 9.9(329) | TAA | 2.5(83) | TGA | 0.6(21) |
| TTG | 16.2(536) | TCG | 7.2(237) | TAG | 0.7(23) | TGG | 12.7(420) |
| CTT | 9.9(327) | CCT | 14.3(472) | CAT | 8.7(289) | CGT | 15.9(525) |
| CTC | 17.0(564) | CCC | 13.7(453) | CAC | 16.2(535) | CGC | 15.1(500) |
| CTA | 6.8(226) | CCA | 13.4(445) | CAA | 16.2(535) | CGA | 5.3(175) |
| CTG | 24.5(810) | CCG | 7.7(255) | CAG | 21.8(723) | CGG | 3.6(118) |
| ATT | 15.5(512) | ACT | 13.6(451) | AAT | 12.8(424) | AGT | 8.1(267) |
| ATC | 28.9(958) | ACC | 17.2(569) | AAC | 27.8(921) | AGC | 10.7(354) |
| ATA | 7.6(253) | ACA | 11.9(393) | AAA | 26.7(883) | AGA | 11.8(392) |
| ATG | 27.3(902) | ACG | 8.8(290) | AAG | 53.1(1757) | AGG | 13.5(446) |
| GTT | 14.7(488) | GCT | 26.3(872) | GAT | 21.8(723) | GGT | 22.0(728) |
| GTC | 20.4(676) | GCC | 21.1(697) | GAC | 32.3(1070) | GGC | 19.9(659) |
| GTA | 12.3(406) | GCA | 12.4(411) | GAA | 27.2(901) | GGA | 18.2(603) |
| GTG | 24.8(822) | GCG | 12.2(404) | GAG | 34.1(1128) | GGG | 4.3(141) |

Coding GC 50.58% 1st letter GC 53.42% 2nd letter GC 39.40% 3rd letter GC 58.93%

TABLE 2

Codon usage table *Autographa californica* multiple nucleopolyhedrovirus (AcMNPV) based on 277 coding sequences (77487 codons)
fields: [triplet] [frequency: per thousand] ([number])

| | | | | | | | |
|---|---|---|---|---|---|---|---|
| UUU | 37.6(2916) | UCU | 10.3(799) | UAU | 22.2(1721) | UGU | 11.2(865) |
| UUC | 11.3(879) | UCC | 7.2(556) | UAC | 26.1(2019) | UGC | 12.5(967) |

TABLE 2-continued

Codon usage table *Autographa californica* multiple nucleopolyhedrovirus
(AcMNPV) based on 277 coding sequences (77487 codons)
fields: [triplet] [frequency: per thousand] ([number])

| | | | | | | | |
|---|---|---|---|---|---|---|---|
| UUA | 20.6(1594) | UCA | 7.2(557) | UAA | 2.7(209) | UGA | 0.5(38) |
| UUG | 34.3(2659) | UCG | 14.2(1100) | UAG | 0.4(29) | UGG | 7.5(579) |
| CUU | 8.2(637) | CCU | 8.2(636) | CAU | 10.2(789) | CGU | 8.1(630) |
| CUC | 7.2(555) | CCC | 11.3(879) | CAC | 12.8(991) | CGC | 13.2(1024) |
| CUA | 8.2(632) | CCA | 8.0(621) | CAA | 26.6(2063) | CGA | 7.4(576) |
| CUG | 13.0(1007) | CCG | 12.7(985) | CAG | 11.5(892) | CGG | 3.9(304) |
| AUU | 31.2(2416) | ACU | 12.4(962) | AAU | 34.5(2671) | AGU | 10.3(800) |
| AUC | 14.3(1111) | ACC | 13.5(1043) | AAC | 44.3(3433) | AGC | 16.1(1251) |
| AUA | 19.7(1527) | ACA | 12.4(961) | AAA | 52.4(4057) | AGA | 9.7(748) |
| AUG | 26.7(2071) | ACG | 18.5(1434) | AAG | 18.3(1418) | AGG | 4.0(309) |
| GUU | 16.5(1277) | GCU | 11.0(850) | GAU | 25.4(1968) | GGU | 7.8(603) |
| GUC | 11.7(904) | GCC | 15.4(1196) | GAC | 33.8(2619) | GGC | 16.1(1251) |
| GUA | 12.6(973) | GCA | 10.0(771) | GAA | 37.2(2885) | GGA | 7.0(541) |
| GUG | 25.7(1990) | GCG | 16.3(1261) | GAG | 16.2(1253) | GGG | 2.9(225) |

Coding GC 41.86% 1st letter GC 43.60% 2nd letter GC 32.68% 3rd letter GC 49.29%

---

The invention claimed is:

1. An insect cell comprising a baculoviral vector comprising:
   (i) a first nucleotide sequence encoding a first amino acid sequence of a parvoviral Rep52 protein and is selected from the group consisting of:
      (a) SEQ ID NO:1;
      (b) SEQ ID NO:5;
      (c) A sequence of at least 75% identity with SEQ ID NO:2;
      (d) A sequence of at least 60% identity with SEQ ID NO:3;
      (e) A sequence of at least 70% identity with SEQ ID NO:4;
      (f) A sequence of at least 85% identity with SEQ ID NO:10;
      (g) A nucleotide sequence complementary to the full length sequence of any of (a)-(f); and
      (h) A nucleotide sequence that differs from the sequence of any of (c)-(f) due to degeneracy of the genetic code; and
   (ii) a second nucleotide sequence encoding a second amino acid sequence of a parvoviral Rep78 protein or a Rep68 protein,
   wherein the first and the second amino acid sequences comprise a homologous region of at least 100 amino acid residues with at least 90% identity beginning at the second residue and ending at the C-terminal residue of the parvoviral Rep 52, and wherein the portion of the first nucleotide sequence that encodes the homologous region and the portion of the second nucleotide sequence that encodes the homologous region are less than 90% identical.

2. The insect cell according to claim 1, wherein the homologous regions in the first and second amino acid sequences share at least 99% amino acid sequence identity.

3. The insect cell according to claim 1, wherein
    (i) the portion of the first nucleotide sequence that encodes the homologous region has an improved codon usage bias for the insect cell as compared to the portion of the second nucleotide sequence that encode the homologous region, or
    (ii) the portion of the second nucleotide sequence that encodes the homologous region has an improved codon usage bias for the insect cell as compared to the portion of the first nucleotide sequence that encodes the homologous region.

4. The insect cell according to claim 1, wherein the difference in codon adaptation index between the nucleotides of the first and the second nucleotide sequences that encode the homologous region is at least 0.2.

5. The insect cell according to claim 3, wherein the nucleotide sequence with the improved codon usage bias comprises a continuous stretch of at least 25 codons all of which are common codons as listed in Table 1 or Table 2.

6. The insect cell according to claim 5, wherein all the codons in the nucleotide sequence with the improved usage bias are common codons as listed in Table 1 or Table 2.

7. The insect cell according to claim 1, wherein at least 50% of codons in the portion of the second nucleotide sequence that encodes the homologous region are altered compared to the corresponding codons in the first nucleotide sequence to maximize AT- or GC-content of the second nucleotide sequence.

8. The insect cell according to claim 1, wherein the first and second nucleotide sequences are part of two separate nucleic acid constructs wherein each of the first and the second nucleotide sequence are operably linked to an expression control sequence for expression in said insect cell.

9. The insect cell according to claim 1, wherein the first and second nucleotide sequences are part of a single nucleic acid construct wherein each of said sequences is operably linked to a respective expression control sequence for expression in said insect cell.

10. The insect cell according to claim 1, wherein the parvoviral Rep proteins are adeno-associated virus (AAV) Rep proteins.

11. The insect cell according to claim 10, wherein the parvoviral Rep proteins encoded by the first and second nucleotide sequences are of the same serotype.

12. The insect cell according to claim 1, wherein the insect cell further comprises:
    (a) a third nucleotide sequence comprising at least one parvoviral inverted terminal repeat (ITR) sequence; and,
    (b) a fourth nucleotide sequence comprising parvoviral capsid protein-coding sequences operably linked to expression control sequences for expression in an insect cell.

13. The insect cell according to claim 12, wherein the cell further comprises at least a fifth nucleotide sequence encoding a gene product of interest and which fifth nucleotide sequence becomes incorporated into the genome of a parvoviral vector produced in the insect cell.

14. The insect cell according to claim 13, wherein the third nucleotide sequence comprises two parvoviral ITR sequences and wherein the fifth nucleotide sequence is located between the two parvoviral ITR sequences.

15. The insect cell according to claim 12, wherein at least one of the first, second, third and fourth nucleotide sequences are stably integrated in the genome of the insect cell.

16. The insect cell according to claim 12, wherein the parvovirus is AAV.

17. A method for producing a recombinant AAV virion in an insect cell comprising the steps of:
    (a) culturing the insect cell according to claim 12 under conditions such that recombinant AAV virions are produced; and,
    (b) recovering the recombinant AAV virions.

18. The method according to claim 17, further comprising the step of affinity-purification of the virion using an immobilized anti-AAV antibody.

19. An isolated nucleic acid construct comprising the first and the second nucleotide sequence according to claim 1.

20. A method for producing a recombinant AAV virion in an insect cell comprising the steps of:
    (a) culturing the insect cell of claim 1 in which all of said Rep proteins are AAV Rep proteins, which cell further comprises
        (i) a third nucleotide sequence comprising at least one AAV inverted terminal repeat (ITR) sequence; and,
        (ii) a fourth nucleotide sequence comprising AAV capsid protein-coding sequences operably linked to expression control sequences for expression in said insect cell
    under conditions such that a recombinant AAV vector is produced,; and,
    (b) recovering the recombinant AAV vector.

21. The method according to claim 20, wherein the nucleic acid construct for expression of the Rep78 or Rep68 protein and the Rep52 protein comprises a single coding sequence for expression of both the Rep78 or Rep68 protein and the Rep52 protein, and wherein the coding sequence further comprises one or more of the following characteristics:
    (a) one, more or all ATG sequences that occur between the translation starts of the Rep78 and Rep68 protein and between the translation starts of the Rep52 protein are eliminated;
    (b) context of the translation initiation codon of the Rep52 protein is optimized in accordance with the optimal initiator context of 5'-N-N-N-N-N-N-A-U-G A-a/c/g-N-3' for efficient translation initiation in said insect cell;
    (c) an expression control sequence comprising a nine nucleotide sequence of
        (i) SEQ ID NO:9 or
        (ii) a nucleotide sequence substantially homologous to SEQ ID NO:9,
    is present upstream of the initiation codon for the Rep52 protein; and,
    (d) the portion of the sequence that encodes the Rep52 protein has an improved codon usage bias for the insect cell as compared to the portion of the coding sequence between the translation starts of the Rep78/68 and Rep52 proteins.

22. The method according to claim 20, wherein the insect cell comprises an additional coding sequence for the Rep52 or Rep40 protein that is operably linked to a promoter that drives expression of the coding sequence in the insect cell, and wherein the coding sequence for Rep52 or Rep40 protein comprises one or more of the following characteristics:
  (a) a stronger promoter for the Rep52 or Rep40 protein-coding sequence as compared to the promoter for the Rep78 or Rep68 protein-coding sequence;
  (b) a higher copy number of the Rep52 or Rep40 protein-coding sequence as compared to that of the Rep78 or Rep68 protein-coding sequence;
  (c) an improved codon usage bias of the Rep52 or Rep40 protein coding sequence for expression in insect cells;
  (d) context of the translation initiation codon of the Rep52 or Rep40 protein is optimized in accordance with the optimal initiator context of

```
5'-N-N-N-N-N-N-A-U-G A-a/c/g-N-3'
``` for efficient translation initiation in said insect cell; and
  (e) present upstream of the initiation codon for the Rep52 or Rep40 protein is an expression control sequence comprising a nine nucleotide sequence of
    (i) SEQ ID NO:9, or
    (ii) a nucleotide sequence substantially homologous to SEQ ID NO:9.

23. The insect cell according to claim 2 wherein the homologous regions in the first and second amino acid sequences share 100% amino acid sequence identity.

24. The insect cell according to claim 6, wherein all the codons in the nucleotide sequence coding for the homologous region in the nucleotide sequence without the common codons are second most frequent codons as listed in Table 1 or Table 2.

25. The method according to claim 18 wherein the antibody is a single chain camelid antibody or an antigen-binding fragment thereof.

26. The insect cell according to claim 1, wherein at least 300 amino acids of the homologous region have at least 90% sequence identity between the first and second amino acid sequences.

27. The insect cell according to claim 1, wherein at least 350 amino acids of the homologous region have at least 90% sequence identity between the first and second amino acid sequences.

28. The insect cell according to claim 1, wherein the entire homologous region has at least 90% sequence identity between the first and second amino acid sequences.

29. The cell of claim 1 wherein
  (i) the insect cell is a *Spodoptera frugiperda* cell,
  (ii) the baculoviral vector is an *Autographa californica* nucleopolyhedrovirus (AcMNPV) vector.

30. The cell of claim 29, wherein either
  (i) the portion of the first nucleotide sequence that encodes the homologous region has improved codon usage bias for the insect cell as compared to the portion of the second nucleotide sequence that encodes the homologous region, or
  (ii) the portion of the second nucleotide that encodes the homologous region has improved codon usage bias for the insect cell as compared to the portion of the first nucleotide sequence that encodes the homologous region,
wherein the nucleotide sequence with the improved codon usage bias comprises a continuous stretch of at least 25 common codons as listed in Table 1 or Table 2.

* * * * *

UNITED STATES PATENT AND TRADEMARK OFFICE
CERTIFICATE OF CORRECTION

PATENT NO.       : 8,697,417 B2
APPLICATION NO.  : 12/670780
DATED            : April 15, 2014
INVENTOR(S)      : Bakker et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 883 days.

Signed and Sealed this

Twenty-ninth Day of September, 2015

Michelle K. Lee
*Director of the United States Patent and Trademark Office*